US009857299B2

(12) United States Patent
Lear et al.

(10) Patent No.: US 9,857,299 B2
(45) Date of Patent: Jan. 2, 2018

(54) HYDROCARBON SENSING METHODS AND APPARATUS

(71) Applicant: Colorado State University Research Foundation, Fort Collins, CO (US)

(72) Inventors: Kevin Lear, Fort Collins, CO (US); Timothy Erickson, Beaverton, OR (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 15/478,982

(22) Filed: Apr. 4, 2017

(65) Prior Publication Data
US 2017/0212044 A1    Jul. 27, 2017

Related U.S. Application Data

(62) Division of application No. 14/889,839, filed as application No. PCT/US2014/037290 on May 8, 2014, now Pat. No. 9,739,709.
(Continued)

(51) Int. Cl.
*G02B 6/00* (2006.01)
*G01N 21/41* (2006.01)
(Continued)

(52) U.S. Cl.
CPC ......... *G01N 21/4133* (2013.01); *G01M 11/33* (2013.01); *G01N 33/1833* (2013.01);
(Continued)

(58) Field of Classification Search
CPC .. G02B 6/028; G02B 6/12004; G02B 6/1221; G02B 6/4291; G02B 27/56;
(Continued)

(56) References Cited

U.S. PATENT DOCUMENTS 5,166,988 A    11/1992    Bobb et al.
5,577,137 A    11/1996    Groger et al.
(Continued)

FOREIGN PATENT DOCUMENTS

WO    2007030737 A2    3/2007

OTHER PUBLICATIONS

PCT/US2014/037290 International Search Report and Written Opinion dated Sep. 4, 2014, 9 pages.
(Continued)

*Primary Examiner* — Thomas A Hollweg
*Assistant Examiner* — Guy Anderson
(74) *Attorney, Agent, or Firm* — Lathrop Gage LLP

(57) ABSTRACT

A chip-scale, reusable sensor can detect aromatic hydrocarbons, such as benzene, toluene, ethylbenzene, and xylenes (BTEX), rapidly in water without sample preparation. The device is capable of real-time, continuous monitoring for BTEX solutes, which diffuse into a film, such as a polymer, on the sensors surface. In operation, BTEX analytes concentrate in the film, causing an increase in refractive index, which modulates evanescent coupling into the chips integrated photodetector array. Integration of the photodetector array simplifies system instrumentation and permits incorporation of an on-chip photocurrent reference region in the immediate vicinity of the sensing region, reducing drift due to temperature fluctuations. In some examples, the chip responds linearly for BTEX concentrations between 1 ppm and 30 ppm, with a limit of detection of 359 ppb, 249 ppb, and 103 ppb for benzene, toluene, and xylene in water, respectively.

9 Claims, 18 Drawing Sheets

Related U.S. Application Data

(60) Provisional application No. 61/821,161, filed on May 8, 2013, provisional application No. 61/862,286, filed on Aug. 5, 2013.

(51) Int. Cl.
    *G01N 33/18*      (2006.01)
    *G01M 11/00*      (2006.01)
    *G02B 6/122*      (2006.01)
    *G02B 6/12*      (2006.01)

(52) U.S. Cl.
CPC ... *G02B 6/1221* (2013.01); *G01N 2021/4166* (2013.01); *G01N 2201/0873* (2013.01); *G02B 2006/12138* (2013.01)

(58) Field of Classification Search
CPC .......... G02B 2006/12123; G02B 2006/12138; G01N 21/4133
USPC ...................................................... 385/12–13
See application file for complete search history.

(56) References Cited

U.S. PATENT DOCUMENTS

| | | | | |
|---|---|---|---|---|
| 7,489,835 | B1* | 2/2009 | Xia | G01N 21/774 385/12 |
| 8,320,728 | B2* | 11/2012 | Mizaikoff | G01N 21/7703 250/227.11 |
| 8,349,605 | B1 | 1/2013 | Lear et al. | |
| 8,554,024 | B2* | 10/2013 | Albert | G01B 11/18 385/12 |
| 2003/0231851 | A1 | 12/2003 | Rantala et al. | |
| 2005/0269490 | A1* | 12/2005 | Loock | G01J 3/42 250/227.14 |
| 2006/0093967 | A1 | 5/2006 | Block et al. | |
| 2006/0210440 | A1* | 9/2006 | Potyrailo | G01N 21/1702 422/82.01 |
| 2008/0219616 | A1 | 9/2008 | Wimberger-Friedl et al. | |
| 2009/0041404 | A1* | 2/2009 | Stoddart | B82Y 15/00 385/12 |
| 2009/0263072 | A1* | 10/2009 | Albert | G01B 11/18 385/13 |
| 2012/0018167 | A1* | 1/2012 | Konopczynski | E21B 47/102 166/369 |
| 2012/0021525 | A1* | 1/2012 | Fehr | B01L 3/502707 436/94 |
| 2012/0170023 | A1* | 7/2012 | Szobota | G01N 21/552 356/51 |
| 2014/0002821 | A1* | 1/2014 | Albert | G01B 11/18 356/364 |
| 2015/0303723 | A1* | 10/2015 | Raghavan | H02J 7/0052 320/107 |

OTHER PUBLICATIONS

Podgoresk, R.P. et al., Selective optical detection of aromatic vapors, Feb. 1, 2002, vol. 41, No. 4, Applied Optics, 601-608.
Extended European Search Report for EP 14794194 dated Nov. 4, 2016, 10 pp.

* cited by examiner

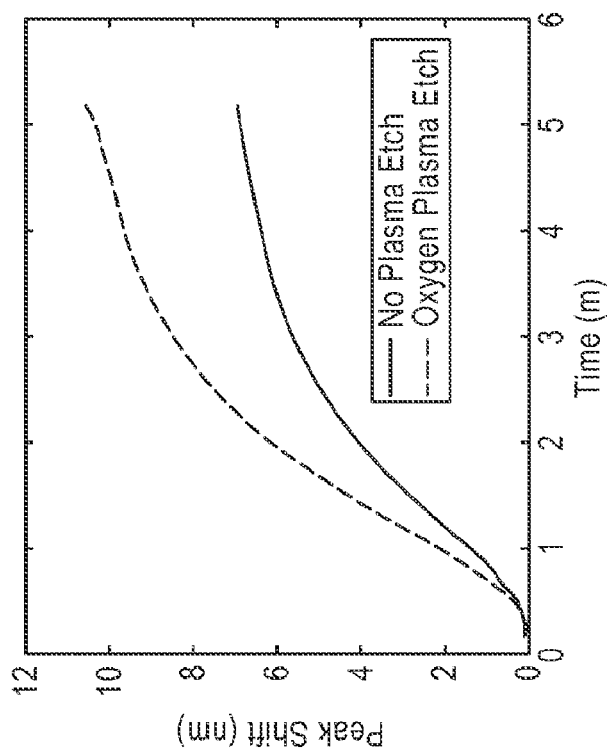
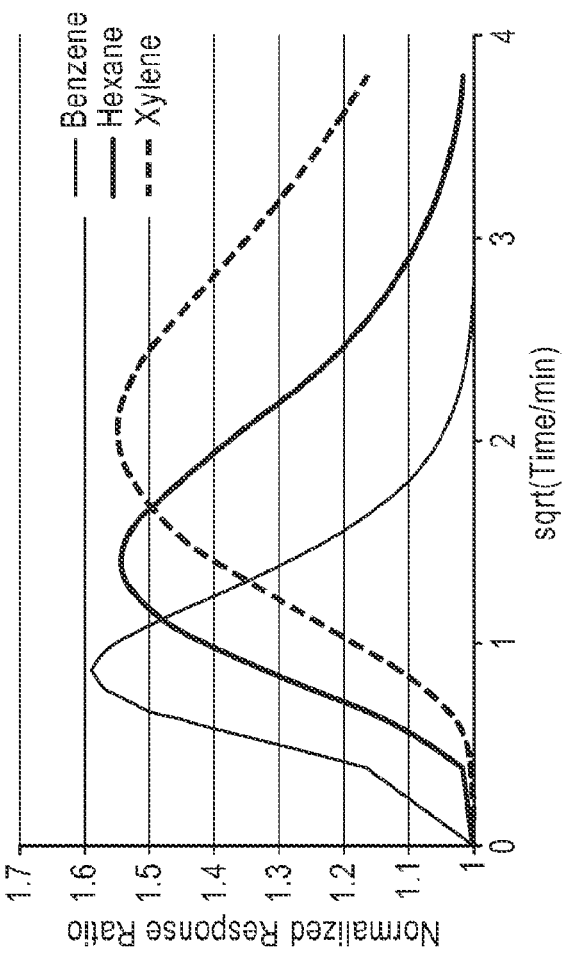
FIG. 2D
FIG. 2C

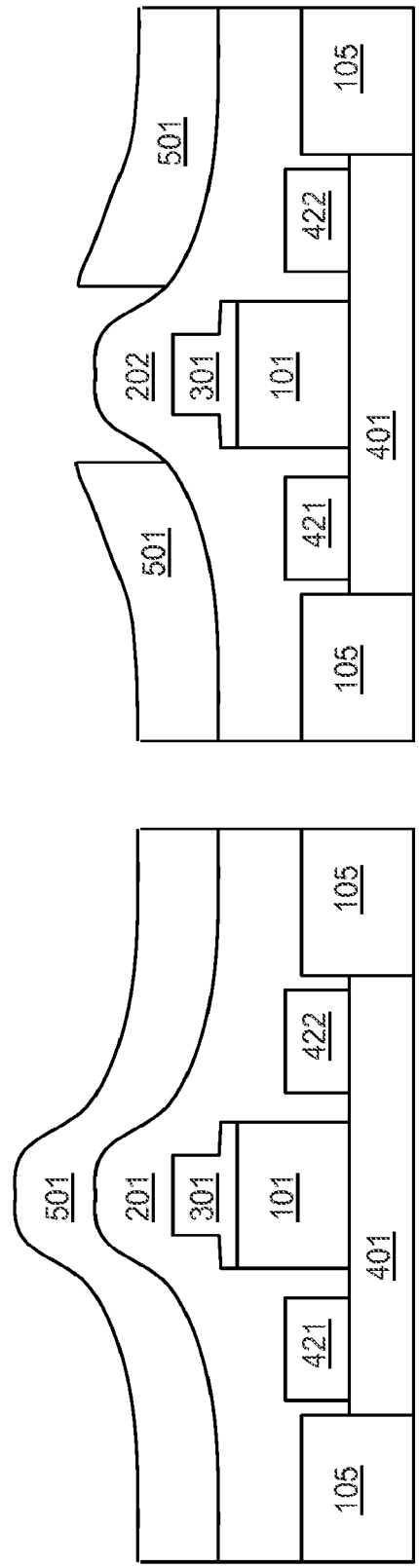

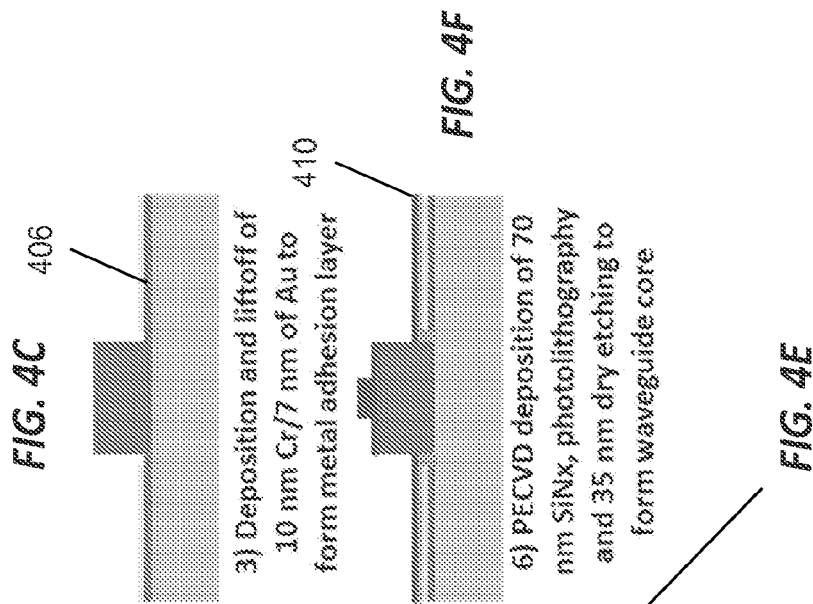

FIG. 4A

1) N-type (1-5 ohm-cm) Si wafer with 1700 nm of thermal oxide

FIG. 4B

2) Photolithography and BOE etch 1600 nm to form oxide buffer layer/lower cladding

FIG. 4C

3) Deposition and liftoff of 10 nm Cr/7 nm of Au to form metal adhesion layer

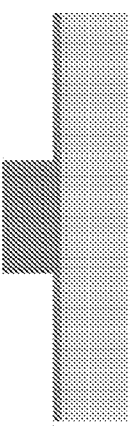

FIG. 4D

4) Photolithography and BOE etch to expose Si for MSM contacts

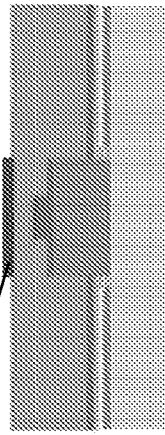

FIG. 4E

6) PECVD deposition of 70 nm SiNx, photolithography and 35 nm dry etching to form waveguide core

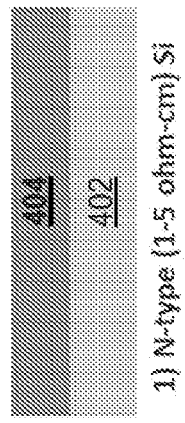

FIG. 4F

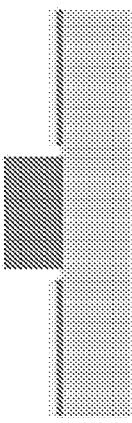

FIG. 4G

5) Deposition and liftoff of 35 nm Au/20 nm Cr/75 nm Al to form MSM contacts and probe pads

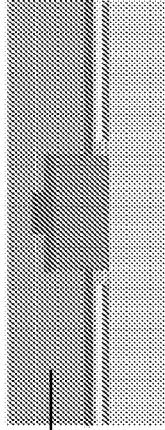

7) Spin coat and cure 6 microns of Teflon AF 1600

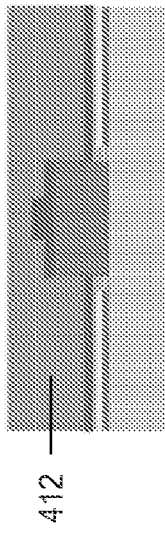

FIG. 4H

8) Deposition and liftoff of 200 nm of Al to form BTEX blocking layer over reference region only. Dry etch sensing region Teflon to 1200 nm thickness

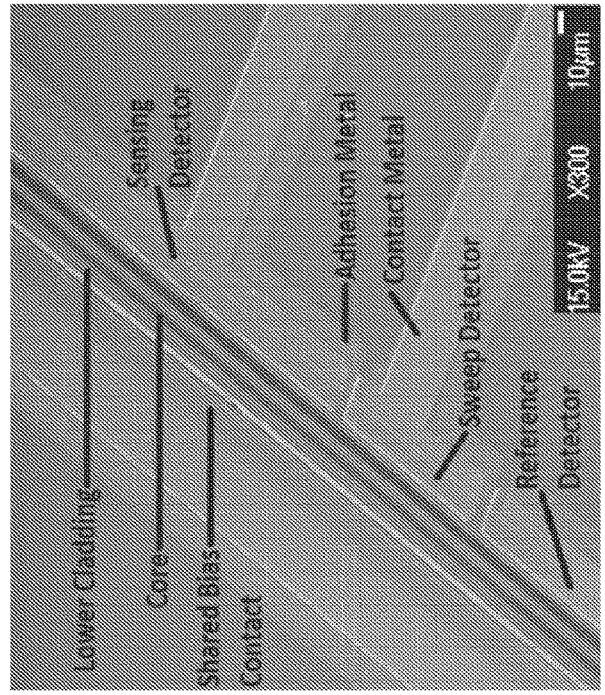
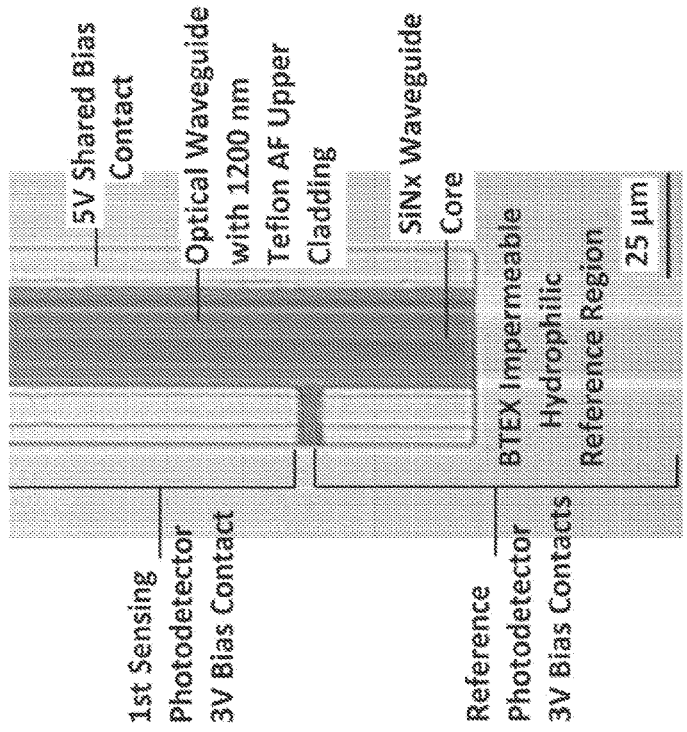
FIG. 5A
FIG. 5B

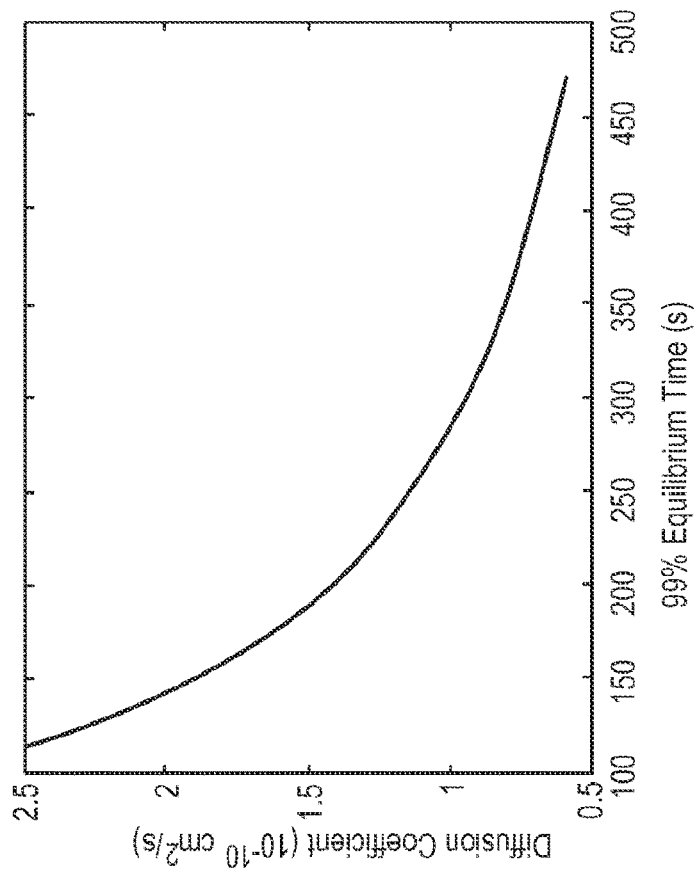
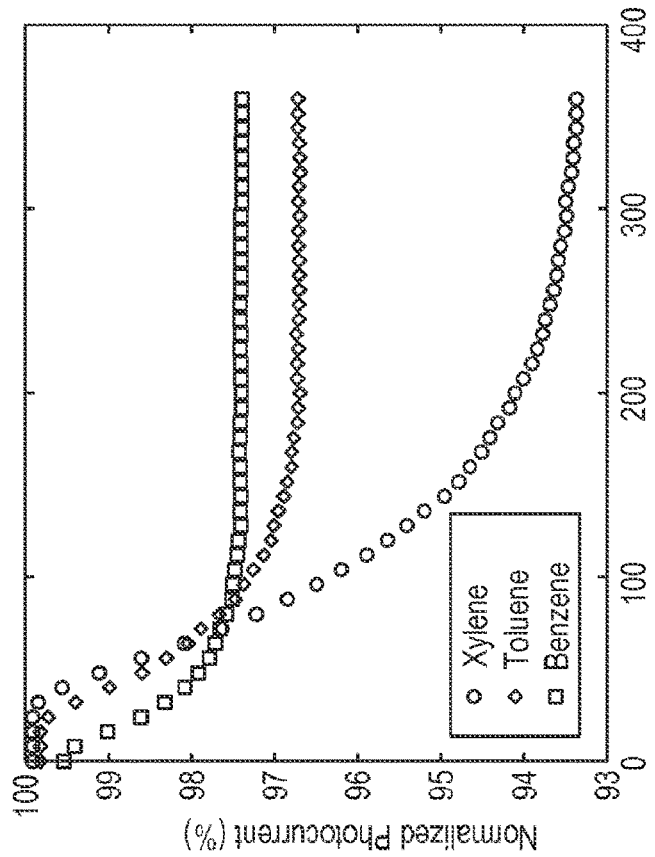
FIG. 13
FIG. 12

HYDROCARBON SENSING METHODS AND APPARATUS

CROSS-REFERENCE TO RELATED PATENT APPLICATION

This application is a divisional of U.S. application Ser. No. 14/889,839, filed Nov. 7, 2015, and entitled "Hydrocarbon Sensing Methods and Apparatus," which is a national phase entry under 35 U.S.C. §371 of PCT/US2014/037290 filed on May 8, 2014, and entitled "Hydrocarbon Sensing Methods and Apparatus," which claims priority under 35 U.S.C. §119(e), from U.S. Application No. 61/821,161, filed May 8, 2013, and entitled "Multi-Analyte Optical Sensor," and also claims priority under 35 U.S.C. §119(e), from US Application No. 61/862,286, filed Aug. 5, 2013, and entitled "Optoelectronic Contaminant Sensor," all of which applications are hereby incorporated herein by reference in their entirety.

This application also claims priority, under 35 U.S.C. §119(c), from U.S. Application No. 61/862,286, filed Aug. 5, 2013, and entitled "Optoelectronic Contaminant Sensor," which application is hereby incorporated herein by reference in its entirety.

BACKGROUND

Aromatic hydrocarbons such as benzene, toluene, ethylbenzene, and xylene (BTEX) are carcinogenic and hazardous to unman health even at relatively low concentrations. To ensure the safety of Municipal water supplies, the Environmental Protection Agency (EPA) has mandated maximum allowable concentrations of 5 ppb, 1 ppm, 700 ppb and 10 ppm for BTEX, respectively. In recent years, industrial activities related to hydrocarbon production, processing, and transportation have resulted in BTEX contamination of water supplies. For instance, pipeline leaks have resulted in benzene contamination of groundwater in Parachute, Colo., and well water in Jackson, Wis. Additionally, hydraulic fracturing activity has been indicated as the cause of BTEX and gasoline-range organic contamination of the Pavilion, Wyo. aquifer.

Due to the increased health risks and remediation costs associated with larger contamination events, there is a strong motivation to develop portable, low-cost technologies, which can automatically sense BTEX contaminants and localize contamination events in real-time. Current state-of-the art sensing technologies such as gas chromatography-mass spectrometry (GC-MS) and gas chromatography-flame ionization detector (GC-FID) can selectively detect BTEX contaminants with exquisite sensitivity at ppt concentrations. However, due to cost, size, and energy requirements, these systems are not typically deployed in the field as real-time monitoring systems. Current monitoring methods typically involve sample collection in the field and transport back to a lab where the assay can be performed, resulting in delayed results and increased analysis costs.

SUMMARY

Embodiments of the present invention include an apparatus and method for sensing a hydrocarbon in a fluid, such as a gas or liquid. In one example, the apparatus comprises a waveguide, which in turn comprises a core, a first cladding layer disposed on a first side of the core, and a second cladding layer disposed on a second side of the core. The second cladding layer includes a continuous film of at least one hydrophobic polymer, such as Teflon. This continuous film defines (i) a first measurement region that has a first surface with a first hydrophobicity and (ii) a second sensing region that has a second surface with a second hydrophobicity greater than the first hydrophobicity. The apparatus also includes at least one first photodetector disposed opposite the core from the first measurement region and at least one second photodetector disposed opposite the core from the second sensing region. In operation, the first photodetector senses an intensity of light evanescently coupled out of the waveguide in the first measurement region. And the second photodetector sense a change in intensity of light evanescently coupled out of the waveguide in the second sensing region due to a change in refractive index in the hydrophobic polymer caused by diffusion of the hydrocarbon into the hydrophobic polymer via the second surface.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and, or structurally similar elements).

FIG. 2C is a plot of normalized response ratio versus the square root of measurement time for a thin film exposed to benzene, hexane, and xylene solutions.

FIG. 2D is a plot of surface resonance plasma peak shift for oxygen-plasma etched films (dashed line) and unetched thin films (solid line) exposed to 30 ppm solutions of benzene.

FIGS. 3A-3D show elevation, top, and end views of an exemplary sensor with an exposed hydrophobic material in a hydrocarbon measurement region and hydrophilic barriers on reference measurement regions.

FIGS. 4A-4H illustrate a process of fabricating an exemplary multi-analyte sensor.

FIG. 5A is an optical microscope image of the reference and sensing regions of an exemplary multi-analyte sensor fabricated using the process of FIGS. 4A-4H.

FIG. 5B is a scanning electron microscope image of an exemplary multi-analyte sensor taken before Teflon AF and reference region patterning in the process of FIGS. 4A-4H.

FIG. 12 is a plot of the normalized photocurrent versus time for a sensor exposed to 30 ppm solutions of benzene (squares), toluene (diamonds), and xylene (circles).

FIG. 13 is a plot of the diffusion coefficient versus equilibrium time for a sensor with a hydrocarbon sensing region that includes 1200 nm thick hydrophobic polymer (e.g., Teflon).

DETAILED DESCRIPTION

Figure 1:
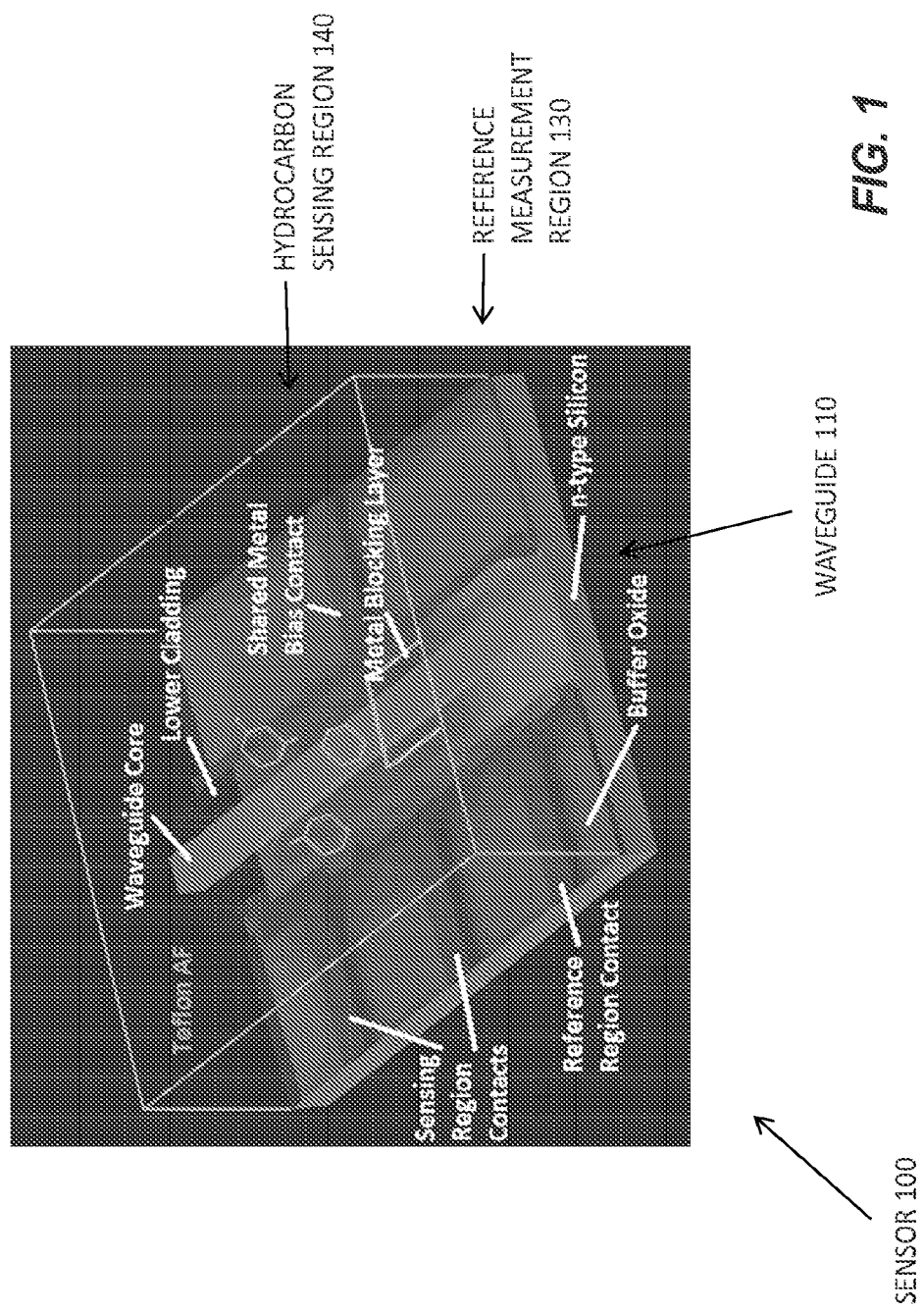
FIG. 1 is a perspective view of an exemplary multi-analyte sensor that detects changes in hydrocarbon concentration based on changes in refractive index caused by hydrocarbon diffusion.

Embodiments of the present invention relate to sensing of impurities or contaminants in impure mixtures using one or more materials whose optical properties change when exposed to the contaminants. An example of such a mixture of interest is aromatic hydrocarbon contamination dissolved in water. In some embodiments, the materials concentrate the impurities, and in some embodiments the surface of the materials exposed to the impure mixtures is textured to enhance the concentration of impurities. Optical properties of the materials of primary interest include refractive index and absorption. Appropriate optical sensing architectures include those that transduce a change in refractive index to a change in photocurrent of one or more photodetectors as a result of a change in the optical power intercepted by those photodetectors.

For some applications, compactness of the sensor is an advantage, and in such cases miniature optical waveguide sensors are attractive solutions. Optical waveguide sensors intended for transducing changes in optical properties of a material can also be influenced by other changes including, for example, changes in optical source power, temperature, optical properties of waveguide or photodetector components due to age or environmental variables, and properties of the mixture to be measured other than the desired impurity concentration. These parameters may also affect optical sensors that do not incorporate waveguides. Hence it can be beneficial to sense the optical properties of materials exposed to impurities of interest with optical sensors that include reference regions that respond to changes such as optical source power and temperature but have a reduced sensitivity to the concentration of target impurities.

For example, a compact optical waveguide sensor may contain at least one reference region and at least one sensing region where at least the sensing region incorporates a material whose refractive index changes in response to the concentration of impurities in a sample mixture where the reference region is less responsive to the concentration of impurities. To obtain beneficial optical waveguide properties, and more comprehensive compensation measurements from the reference region, the sensor may include the same impurity-sensitive material in both the reference and sensing regions, but may be configured to restrict the amount of impurity or the amount of sample mixture containing the impurity that can interact with the reference region. While preventing any amount of impurity from reaching the reference region may simplify the approach for combining the reference region and sensing region photodetector signals, it is not essential to completely eliminate or even mostly eliminate all impurity from reaching the reference region. Designs that allow some impurity to reach the reference region may be simpler to manufacture than those intended to completely eliminate impurity interactions with the reference region.

The reference region may be less responsive to the impurity concentration than the sensing region as specified in various ways including, for example, the magnitude of the equilibrium response or the rate of response. The reference region may also be less responsive when considering combinations of factors such as products or sums of parameters related to sensitivity and temporal response.

Consider for example, the response of a photodetector associated with a reference region that intercepts a variable fraction of the optical power in a waveguide. This variable fraction of the optical power can be a function of the refractive index of an impurity-sensitive material, and the refractive index of the material can be a time-varying function of the amount of impurity that has diffused into the material. An example of such a situation would be an optical waveguide that produces an evanescent optical tail which penetrates into the bottom portion of a layer of hydrophobic polymer, such as Teflon, and where the top of the Teflon, possibly textured, is in contact with a water solution containing dissolved benzene. When the benzene, which has a refractive index $n \approx 1.5$, enters and concentrates in the Teflon, which has a refractive index $n \approx 1.3$, the combined refractive index of the Teflon with benzene rises. Initially, the benzene might enter at the top of the Teflon layer, but from there it can diffuse toward the bottom of the Teflon layer. As the benzene diffuses over time, more of it will move into the evanescent optical tail, raising the refractive index there. As the refractive index in the evanescent optical tail increases, the fraction of optical power intercepted by the photodetector and thus photocurrent can change. This change may occur gradually rather than instantaneously because the diffusion process takes time.

This illustrative example of the photocurrent response to the benzene concentration can be further elucidated with the equations below. The variables used in the equations are:

$C_{sample}$=constant concentration of impurity (e.g., benzene) in the sample beginning at time t=0 (the impurity concentration is assumed to be zero for t≥0);

K=partition coefficient, i.e., the ratio of the concentration of impurity just inside the impurity-sensitive material (e.g., Teflon) to the ratio of the concentration of impurity in the sample;

d=thickness of the impurity-sensitive material layer with coordinate system x=0 being at the bottom of the layer and x=d at the top of the layer (other sensor orientations are also possible);

C(x,t)=concentration of impurity in the impurity-sensitive material as a function of spatial position, x, and time, t (The concentration distribution may change over time due to diffusion);

I(x)=optical intensity (i.e., optical power per unit cross-sectional area) of the waveguide's evanescent optical tail in the impurity-sensitive material;

$C_{WG}(t)$=weighted average concentration of impurity in the waveguide's evanescent tail (mathematically, $C_{WG}(t) = \int_{x=0}^{x=d} I(x)C(x,t)dx / \int_{x=0}^{x=d} I(x)dx$);

$f_{diff}(t) = C_{WG}(t)/(K\, C_{sample})$ is a step response function that is zero for t≥0 and rises toward 1 as impurity diffuses through the layer (in equilibrium, $C_{WG}(t)$=K $C_{sample}$ and thus $f_{diff}(t)$=1);

n=the refractive index of the impurity-sensitive material, which is a function of the impurity concentration in the material;

$P_{tot}$=the total optical power in the waveguide immediately prior to the photodetector;

α=the absorption coefficient associated with coupling optical power from the waveguide to a photodetector;

L=the length of the photodetector;

η=1−exp(−αL), the fraction of the waveguide's power coupled to the photodetector;

I=the photocurrent flowing through the photodetector, which is proportional to η $P_{tot}$;

$I_0$=the photocurrent for t≥0, before impurity enters the impurity-sensitive layer; and R=responsivity of the photodetector, i.e. the ratio of photocurrent to intercepted power.

Using these definitions, the equilibrium sensitivity of the coupling fraction, η, to a change in the sample concentration from zero to $C_{sample}$ is $S_{equil}=(d\eta/dn)(dn/dC_{WG}) K\, C_{sample}$ according to the chain rule of derivatives since the equilibrium change in the concentration of the impurity in the evanescent tail is K $C_{sample}$, and this will change the refractive index in the evanescent tail by $(dn/dC_{WG})$ K $C_{sample}$ and subsequently change the coupling fraction. However, due to the diffusion process, this equilibrium value is an asymptotic limit and the coupling fraction and thus photocurrent change over time. The photocurrent is related to the coupling fraction by I=Rη$P_{tot}$. So the change in photocurrent as a function of time is $I(t)-I_0 = R\, P_{tot}\, S_{equil}\, f_{diff}(t)$.

An example formulation of the relative responsiveness of the reference region and the sensing region can now be given in terms of these mathematical definitions. For example, responsiveness of a reference or sensing region can be given as the absolute value of the product of that region's equilibrium sensitivity, $S_{equil}$, and that region's diffusion step response function, $f_{diff}(t)$. Using this example definition, if at some time, t, $|S_{equil} f_{diff}(t)|$ for the reference region is less than $|S_{equil} f_{diff}(t)|$ for the sensing region, then the reference region can be said to be less responsive than the sensing region.

The rapidity of response of a reference or sensor region as characterized by the diffusion step response function, $f_{diff}(t)$, of that region may be conveniently characterized in terms of a impurity diffusion time. The impurity diffusion time is the length of time required for $f_{diff}(t)$ to rise from zero to some specified value. For example, the 50% impurity diffusion time is the time required to reach $f_{diff}(t)$=0.5, and the exponential diffusion time constant is the time required to reach $f_{diff}(t)=1-e^{-1}$. The terms "impurity diffusion time" and "impurity diffusion time constant" are used interchangeably in this document. In examples where hydrocarbons are the impurity, the impurity diffusion time may also be referred to as the "hydrocarbon diffusion time" or "hydrocarbon diffusion time constant".

CMOS-Compatible, Optoelectronic Sensing Chips

A CMOS-compatible, optoelectronic sensing chip can detect aromatic hydrocarbons, such as benzene, toluene, ethylbenzene, and xylene (BTEX), by measuring changes in refractive index of a portion of waveguide exposed to hydrocarbon solutions. For instance, a sensor can measure the BTEX concentration of contaminated water flowing over the chip's sensing region(s). An exemplary optoelectronic sensing chip can perform broad-based, exclusionary detection of hydrophobic contaminants and at a limit of detection of 359 ppb, 249 ppb, and 103 ppb for benzene, toluene, and xylenes, respectively. In some cases, the chip may also identify the type of contaminant based on a model of the solute's diffusion coefficient.

Unlike other hydrocarbon sensors, waveguide-based, refractive-index sensors can be very compact (e.g., with sensing areas of about 1 square centimeter or less or preferably sensing areas of about 0.1 square mm or less). They can also operate with little to no sample preparation, while offering cost advantages due to system simplification. The proposed waveguide-based sensor provides a method for label-free method for detection of BTEX and other non-polar contaminants in aqueous environments.

Exemplary sensors can be used in oil fields to monitor leaks and spills. They can also be used to monitor water quality, e.g., in homes, offices, hospitals, reservoirs, water treatment facilities, and manufacturing plants. For instance, a construction company may submit weekly water quality reports provided by one or more sensors that test samples from the job site. They can also be used to measure the effectiveness of remediation efforts, e.g., by sensing gasoline range organics and diesel organics at gas stations, spill sites, etc.

Optoelectronic Hydrocarbon Sensors

An exemplary sensor may include an optical waveguide with an upper cladding formed from a thin sensing film whose refractive index changes when the film is exposed to one or more analytes. Typically, the film absorbs the analyte(s) from a sample solution. For example, a hydrophobic film, such as Teflon or another fluorinated polymer, may preferentially absorb nonpolar contaminants, such as BTEX and other hydrocarbons. Consider a film whose refractive index in the absence of the analyte is $n_0$. In the presence of the analyte, the film's refractive index and/or optical absorption coefficient may change, e.g., due to absorption of the analyte, swelling caused by the analyte, or chemical interaction with the analyte, such as various forms of chemical bonding. Changes in the sensing film's absorption coefficient and/or refractive index alter the waveguide's propagation properties. These propagation properties may include attenuation of the optical field due to absorption, change in the effective refractive index of various modes or a spatial redistribution of energy in the guided mode induced by solute-driven refractive index changes in the waveguide's upper cladding.

Changes in the waveguide's propagation properties may be measured using nonintegrated photodetectors to measure the change in the amplitude of a guided wave; using integrated, evanescently coupled photodetectors to measure changes in the spatial redistribution of the optical mode profile, which alters evanescent coupling into a photodetector located immediately beneath the waveguide's lower cladding as described in U.S. Pat. No. 8,349,605, which is incorporated herein by reference in its entirety; or using interferometers (such as Mach-Zehnder, ring, or thin-film interferometers or resonators) to measure changes in phase or in the resonance wavelength of the photonic structure. Other techniques for measuring changes in the film's refractive index include but are not limited to surface plasmon resonance, thin-film interferometry, and ellipsometry.

The depth of optical field penetration into the upper cladding thin film depends on the refractive index of the waveguide core, upper and lower claddings, and the dimensions of these layers. Typically, both the refractive index of the waveguide's upper cladding sensing film and lower cladding would be less than the refractive index of the waveguide core, in order to achieve total internal reflection. Additionally, the waveguide's optimal dimensions, which are dependent on the refractive index of each layer, may be tuned to increase the extent of the evanescent field penetration into the upper cladding sensing film. In some cases, this increases the sensitivity of the device.

FIG. 1 illustrates an integrated optical waveguide sensor 100 that includes a single-mode silicon dioxide/silicon nitride ($SiO_2/SiN_x$) optical waveguide 110 formed on an n-type silicon substrate 102. The optical waveguide 110 includes a waveguide core 112 on a lower cladding 114 whose refractive index is lower than that of the waveguide core 112. The optical waveguide 110 also includes an upper cladding 116 formed of a hydrophobic polymer—in this case, plasma-etched superhydrophobic Teflon AF 1600, which has a refractive index of about 1.31. An exposed portion of the upper cladding 116 forms a hydrocarbon sensing region 140, which preferentially concentrates hydrophobic BTEX contaminants at factors exceeding two orders of magnitude. Other polymers may be used for portions or all of the upper cladding 116 including trifluoroethylacrylate, hexylmethacrylate, chlorophenylacrylate, and combinations thereof (e.g., 82% hexylmethacrylate/18% chlorophenylacrylate).

The sensor 100 also includes one or more reference measurement regions 130 thatf can be used to correct for temperature fluctuations, device variability, coupling efficiency, and other sources of drift. The device may incorporate reference regions in specific locations along the waveguide structure, which contain a blocking layer over the upper cladding. In FIG. 1, for example, an impermeable metal blocking layer 120 inhibits nonpolar solutes from diffusing into the upper cladding 116 in the reference region 130. In one embodiment, the metal blocking layer 120 is formed by depositing a 300 nm layer of titanium metal over the reference region 130 to inhibit solute diffusion into the reference region 130. When the titanium is oxygen plasma etched, a hydrophilic layer of titanium oxide is formed on the outermost portion of the metal, creating a hydrophilic barrier, which is significantly impermeable to nonpolar analytes. In order to promote titanium adhesion, the Teflon layer (upper cladding 116) may be oxygen plasma etched prior to metal deposition. Oxygen plasma etching may also enhance the upper cladding's uptake of nonpolar solutes in regions not covered by the metal blocking layer 120. This structure may be fabricated using a suitable CMOS process flow, e.g., the process flow 400 shown in FIG. 4.

The waveguide 110 is formed over an integrated metal-silicon-metal (MSM) photodetector array that detects the evanescent tail of the mode guided by the waveguide 110. In some cases, each photodetector in the array has a length of 300 µm and a width of 25 µm. At least one photodetector in the MSM photodetector array is positioned within the reference measurement region 130 and coupled to a reference region contact 134 and to a shared metal bias (common/ground) contact 154. And at least one other photodetector in the MSM photodetector array is positioned within the hydrocarbon sensing region 140 and coupled to a respective sensing region contact 144 and to the shared metal bias (common/ground) contact 154. For instance, the chip 100 may include a total of eight photodetectors: one reference photodetector followed by seven sensing photodetectors.

The optical waveguide 110 is optically coupled to a laser or other light source (not shown). In some cases, the laser is coupled to the waveguide 110 via an optical fiber; in other cases, the laser is integrated directly into the sensor. For instance, the laser may be a flip-chip laser that couples light into the waveguide 110 via a grating (not shown). Other circuitry, including electronic readout circuitry for the MSM photodetector array, could be integrated onto the chip as well to form a lab-on-a-chip groundwater contaminant sensor. For instance, the sensor 100 could include a laser modulation circuit and a lock-in amplifier coupled to the MSM photodetector array to increase the photodetector signal-to-noise ratio (SNR) and to substantially cancel sources of drift that occur on time-scales substantially longer than the reciprocal of the modulation frequency or substantially longer than the reciprocal of the lock-in bandwidth.

In operation, light from a red (660 nm) laser diode (not shown) is end-fire coupled into the chip's optical waveguide 110. (Other wavelengths are also possible, depending on the waveguide design and the analyte being sensed.) At the same time, the hydrocarbon sensing region 140 is exposed to an aqueous solution, such as a water sample, containing the analyte (e.g., BTEX). For instance, the solution may flow over the hydrocarbon sensing region 140 (and possibly the reference measurement region 130 as well); the sensor 100 can also be immersed or covered in the solution or exposed to the solution via one or more microfluidic channels. BTEX solutes (n≈1.5) in the water sample partition from the aqueous phase and diffuse into the upper cladding 116 in the hydrocarbon sensing region 140 at a rate given by the upper cladding's hydrocarbon diffusion constant. This causes the upper cladding's refractive index to increase, which in turn causes guided mode power to shift upward into the upper cladding 116. This in turn leads to a decrease in evanescent coupling into the integrated silicon photodetector located beneath the $SiO_2$ lower cladding 114. The decrease in photodetector coupling causes a decrease in the photocurrent measured at the sensing region contacts 144.

At the same time, the impermeable metal blocking layer 116 inhibits contaminants from diffusing into the Teflon AF upper cladding 120 in the chip's photocurrent reference region 130. If the metal blocking layer 116 is perfectly impermeable, and completely surrounds the reference region 130 then its equilibrium sensitivity is zero; $S_{equil,ref}=0$. The lack of hydrocarbon in the reference region 130 can also be thought of as an infinite hydrocarbon diffusion time. In this case, the photocurrent flowing through the photodetector(s) in the reference measurement region 130 does not change as a function of contaminant concentration. (In practice, the metal blocking layer 116 may be somewhat permeable, giving the reference measurement region 130 a small equilibrium sensitivity or a large, but not infinite, hydrocarbon diffusion time that is greater than that of the hydrocarbon measurement region 140.) Nevertheless, photocurrent flowing through the photodetector(s) in the reference measurement region 130 may fluctuate as a function of laser diode temperature, age, coupling efficiency and waveguide temperature, etc. Thus, it acts as a reference signal that can be compared to (e.g., subtracted front, dividing, or divided by) the photocurrent(s) generated by the photodetector(s) in the sensing region 140 in order to yield a more sensitive measurement of the change in the upper cladding's refractive index as a function of contaminant concentration.

The sensor 100 may be coupled to a processor and/or a memory (not shown) that process and store, respectively, the signals from the photodetectors. The processor and memory may be coupled to the photodetectors via the reference region contacts 134 and the sensing region contacts 144. In operation, the processor may compare one or more sensing signals to one or more reference signals, and/or compute the concentration (and/or change in concentration) of one or more contaminants based on the difference between or ratio of the reference region signals and the sensing region signals. The processor may also identify different types of contaminants, e.g., by monitoring absolute signal levels, relative signal levels, changes in absolute or relative signal levels, and/or rates of change in absolute or relative signal levels provided by one or more of the photodetectors in the sensor 100. The processor may generate status or alarm signals by comparing computed values to threshold values which may be stored in memory.

Thin Films for Optoelectronic Hydrocarbon Sensors

As noted above, the sensing film in the waveguide's upper cladding can have a native refractive index that is different than that of the solutes to be detected. The solutes may also have a different refractive index than water. Diffusion of BTEX solutes ($n \approx 1.50$) into the immobilized film produces an increase the film's bulk refractive index. The change in refractive index versus time enables measurement of the solute's concentration and the solute's diffusion coefficient, thereby providing enhanced ability to distinguish different solutes at unknown concentrations.

Examples of thin films that preferentially absorb hydrocarbons, including polyaromatic and aromatic hydrocarbons like BTEX, include hydrophobic materials, such as many polymers. One embodiment is the use of specialized Teflon AF films, which have been chemically and/or physically enhanced for sensing BTEX contaminants. Teflon AF has a very low refractive index ($n \approx 1.31$) and has a large fractional free volume, so that its index readily increases when higher index hydrocarbons $n \approx -1.5$ diffuse into the film.

Thin polymer films made from other materials may be used for sensing polar molecules in water. And multiple compositions of films may be implemented on a single chip or system so that separate sensing measurements can be made of the refractive index change of the different material compositions. If the different material compositions or different polymers are chosen to more strongly partition certain groups of molecules from water or other solvents, the specificity of the sensing system can be enhanced. The different material compositions may all absorb or respond to multiple impurities, also known as analytes, but to differing degrees. Methods such as chemometrics may be employed to use the responses of multiple material compositions to multiple impurities to improve specificity.

While specific examples are offered here for sensing non-polar hydrocarbons in water, sensors may also be implemented with other sensing films, such as hydrophilic ones, for detecting or quantifying polar contaminants or impurities in non-polar fluids. For example, water moisture contamination of oils or hydrocarbon fuels could be performed with an appropriate version of the invention. Again, many methods for modifying the surface free energy and accordingly the hydrophilicity or hydrophobicity, including superhydrophilicity or superhydrophobicity, of polymer, hydrocarbon, metal, metal-oxide, insulator, or dielectric materials are known to those skilled in the art of solid-state materials surface modifications. And these methods may he practiced to alter the contact (wetting) angles or surface free energy of target analytes (e.g., contaminants or impurities) on both the sensing film and the barrier material to enhance the ratio of the partition coefficient of the sensing film to the partition coefficient of the barrier material with respect to the analyte concentration in the sample solution.

Sensing Film Thickness, Diffusion Length, and Diffusion Time

For sensing purposes, the second cladding (sensing film) in the measurement region should be thick enough to prevent the guided mode's evanescent field from extending too far into the medium above the waveguide. For example, if the evanescent optical field, which is proportional to the square-root of optical intensity, arid is decaying according to $E(x)=E_0\exp(-\gamma x)$, where $E_0$ is the field strength at the surface of the second cladding closest to the core and x is the distance perpendicular to that surface, then the thickness of the second cladding should be at least a significant fraction, for example, 10% of the optical penetration distance, defined as $1/(2\gamma)$. The factor of 2 in this expression arises from the square relationship between optical field and intensity. The evanescent decay constant, $\gamma$, is approximately constant for uniform refractive index layers and may be determined by calculations including numerical simulation of the optical fields in waveguides using methods that are well known to those practiced in the art of optical waveguide design.

The upper cladding in the measurement or sensing region should also be thin enough to ensure that the hydrocarbon diffuses far enough over the measurement period to provide a detectable change in refractive index. In other words, the maximal thickness of the hydrophobic polymer should not be so large as to create excessively slow responses/excessively large hydrocarbon diffusion times. For example, if a response from the sensor is desired within a time, T, of a change in the hydrocarbon concentration, then the thickness of the hydrophobic polymer layer should be on the order of or less than the square-root of (DT) where D is the diffusivity, a.k.a. diffusion constant, of the hydrocarbons to be sensed in the hydrophobic polymer.

The claddings in the sensing and reference regions may also be characterized by respective hydrocarbon diffusion times. As used herein, the hydrocarbon diffusion time may be practically defined as the time required for the photodetector signal (or measurement of the same) to change by a specified fraction of the total asymptotic change over very long times, for example, ten times the diffusion time, in response to a change in hydrocarbon concentration or content that is significantly more rapid than the hydrocarbon diffusion time. For example, if the hydrocarbon concentration in an aqueous solution changes over a period of less than approximately 30% of the diffusion time, then the change in the photodetector signal may be considered to be dominated by the diffusion process. This practical definition is intended to be approximately consistent with the mathematical definition provided above, but allow for characterization of diffusion times within a finite time since reaching a true equilibrium state, similar to reaching an asymptotic limit, may require infinite time.

Such relatively rapid changes in concentration may be implemented by a change in the source of the aqueous sample, or rapidly switching the solution being measured between the aqueous sample and a reference aqueous solution that has a controlled hydrocarbon content including potentially a negligible amount of hydrocarbons. The specified fraction of the total asymptotic change is often specified to be $1-e^{-1}$. For example, if the sensor is tested with a system that switches the hydrocarbon concentration over a period of 3 seconds and the resulting signal changes by an amount $\Delta S$ over 100 seconds and the time required for the signal to change by $\Delta S$ ($131\ e^{-1}$) is 10 seconds, then 10 seconds can be taken as the approximate diffusion time since the change in concentration occurred over a period of 30% of the diffusion time and the total change was determined over a period that was 10 times longer than the diffusion time. If this experiment is performed and the definitions are not consistent, then more rapid switching can be implemented using methods known to those practiced in the art of liquid and gas handling, plumbing and switching, and the total change can be determined by monitoring the signal for a longer time until the consistency requirements are met.

In some cases, the film thickness may be about six evanescent decay lengths in order to provide a sensor response time that is short enough to he useful and to limit the evanescent field that extends beyond the sensing film. Thus for a device with a 160 nm decay length, the film may be about 960 nm thick or thicker. While thicker films may have longer sensing times, they may be advantageous for analyte identification based on measurement of the solute's diffusion coefficient. On the other hand, for more rapid the sensor response, the sensing film thickness may be less than six times the decay length. The film thickness should be chosen while considering the optical power distribution, diffusion coefficients of the target analytes, and the desired response time.

The upper cladding's sensing performance can also be defined in terms of the hydrocarbon diffusion length, $L=\sqrt{Dt}$, where t is the time measured from when the analyte solution comes into contact with the sensing region. If the upper cladding's thickness $d \gg L$, the upper cladding's refractive index may not change appreciably over the measurement time, and when $d \ll L$, the upper cladding may become saturated with hydrocarbon before the end of the measurement period. For a given measurement period, the most rapid change in the sensor's response may occur near when the upper cladding thickness and hydrocarbon diffusion length are of the same order of magnitude. Note that the shape of the response can also be somewhat influenced by the optical penetration distance (or equivalently the evanescent decay length) as well as the film thickness and diffusion coefficient of the analyte. For example, if the decay length is much, much less than the film thickness, then the analyte may diffuse through nearly the entire film prior to being close enough to the waveguide core to appreciably affect the propagation of light in the waveguide.

Figure 2A:
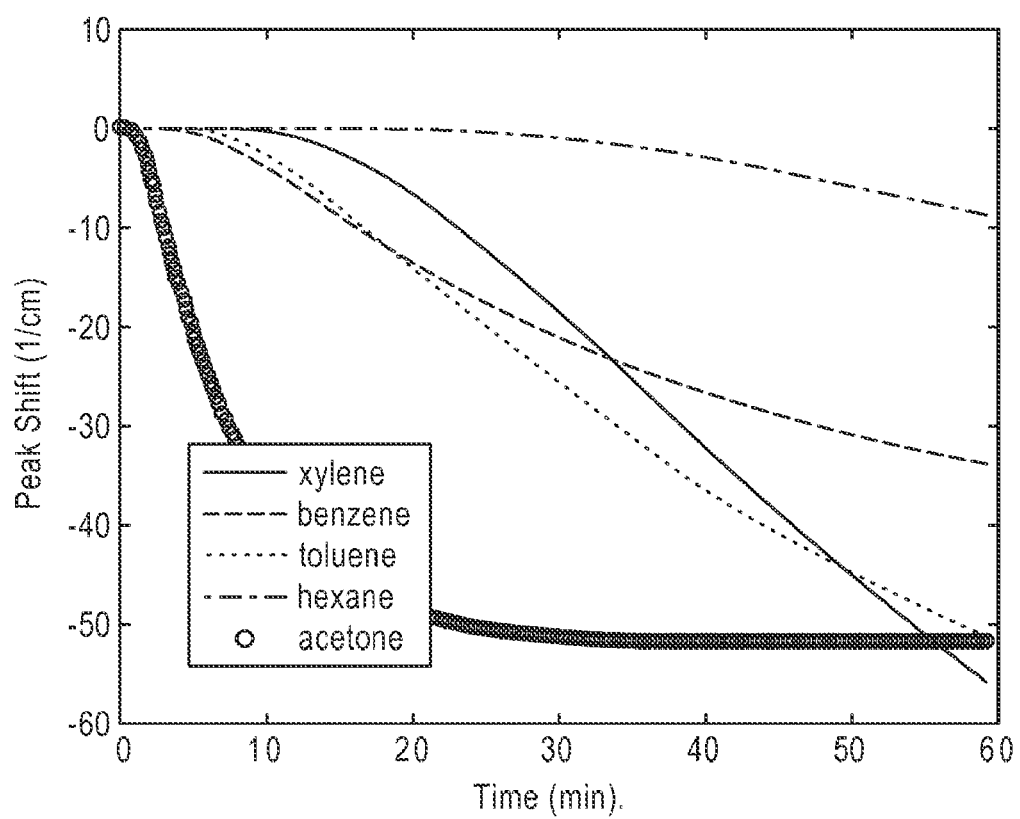
FIG. 2A is a plot of surface resonance plasmon peak shift versus time for a thin film exposed to different hydrocarbons.

FIG. 2A is a plot of peak shift versus time for surface plasmon resonance sensing of a thin film of Teflon AF exposed to different hydrocarbons that illustrates the temporal nature of hydrocarbon diffusion in thin films. In this surface plasmon resonance example, the wavelength of the resonance peak increases as the refractive index of the sensing film layer increases due to hydrocarbon diffusion into the film.

To create curves such as those shown in FIG. 2A, the sensor is exposed to a reference solution free of analytes for a period of time long enough for the response to reach near equilibrium. Such a period of time can be empirically obtained from the temporal response curves as the time required for the signal to approach within, for example, 1% or 0.1%, of the equilibrium value. Alternatively, the amount of time can be calculated or simulated based on the diffusion coefficient, D, and thickness, d, of the film. A useful time unit can be calculated as $T=d^2/D$, and typical waiting times to come close to equilibrium would be several multiples of T, such as on the order of 5T or longer.

If an individual sensor of the type described here is used for continuous, real-time monitoring, it will potentially be exposed to some level of analyte rather than the analyte-free reference solution mentioned above. Also, the level of analyte may be slowly varying at a rate slower than the response shown in FIG. 2A above, making it difficult to determine whether an individual analyte's diffusion constant is dominating the temporal response time, or the slowly varying concentration of the analyte. Hence it could be useful to have sensor systems with sensors that are both continuously exposed to the sample environment to be monitored as well as sensors that are kept in a reference solution or periodically flushed with a reference solution.

In one example mode of operation, if the signal from the continuously monitoring sensor showed a change in concentration of one or more unknown analytes, the same unknown sample solution could be quickly switched, on a time scale much less than T, to another sensor that had been in a reference solution without analytes. Thus a rapid change in the concentration of the unknown analyte would be present at the surface of the sensing film of this second sensor used for distinguishing analytes according to the response time of the analyte across the film.

The signal from the second sensor, similar to one of the curves in FIG. 2A, can be analyzed by methods described below to identify the analyte or narrow the likely analytes down to a group with comparable diffusion coefficients. For emphasis, the vertical magnitude of the change in the curves shown in FIG. 2A, i.e., the maximum change in peak shift as shown in that plot for the example of surface plasmon resonance, would change with analyte concentration, but the temporal shape of the curve, including the steepness of the initial part of the curve (once normalized to the maximum change over times much greater than T) depends on the diffusion coefficient of the analyte in the sensing film.

Different Film Thicknesses for Differential and Multi-Analyte Measurements

Figure 2B:
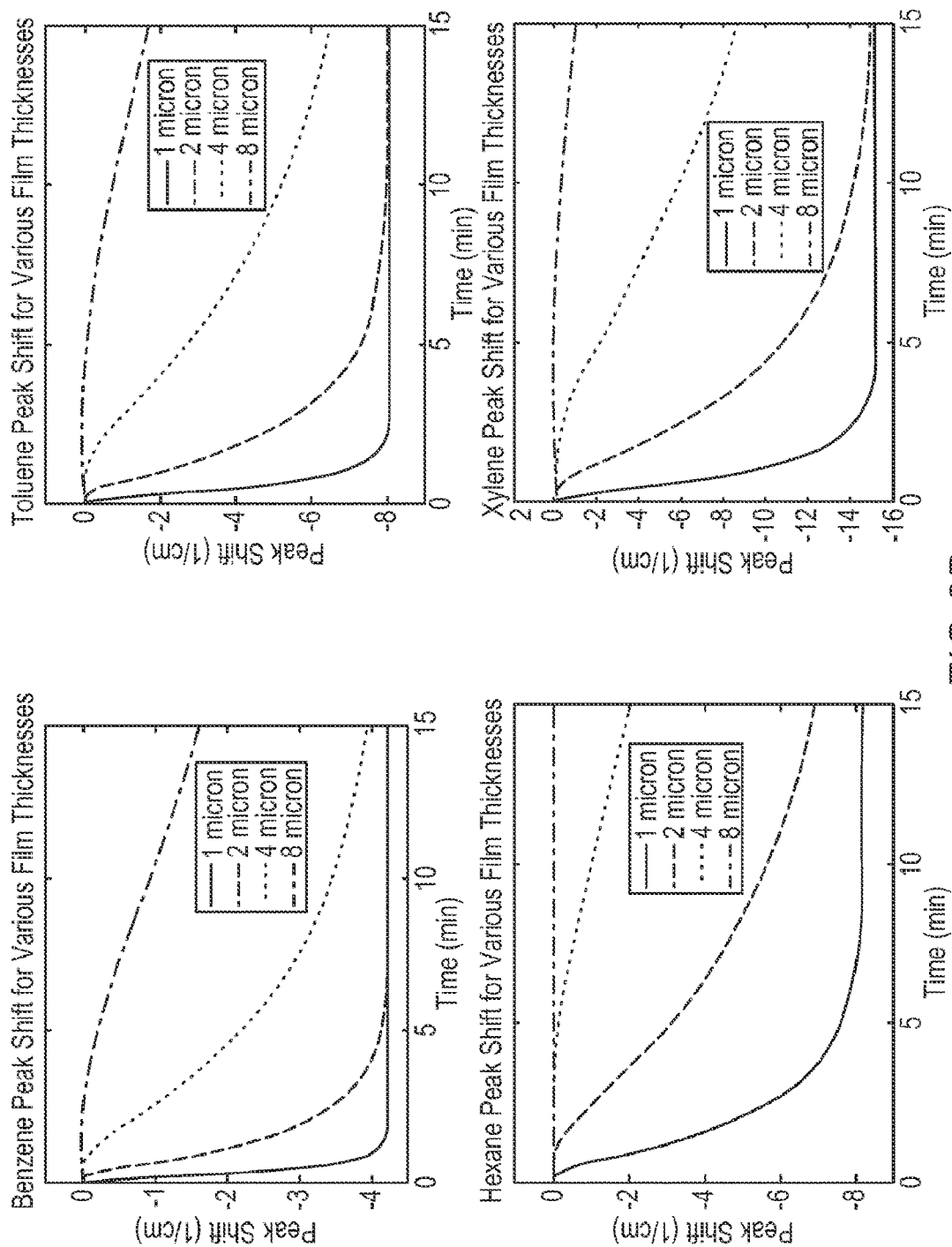
FIG. 2B includes plots of surface resonance plasmon peak shift versus time for a thin films of different thicknesses exposed to different hydrocarbons with concentrations of 1 ppm each.

Surface plasmon resonance analysis also shows that sensors with upper cladding regions of different thicknesses can be used for differential measurements and detecting hydrocarbon type. In FIG. 2B, the peak shift, and hence bulk refractive index change is shown for 1 ppm solutions of benzene, hexane, toluene, and o-xylene at film thicknesses of 1, 2, 4, and 8 microns. Multiple thicknesses can be used to generate a series of curves for more robust curve fitting. The surface plasmon instrument properties used to generate these curves arc based on a measured responsivity of $9.37 \times 10$ refractive index units per wavenumber. For the experiments shown below, the starting resonance peak waveguide number was 9615 $cm^{-1}$ or approximately 1040 nm.

Surface plasmon resonance is offered as an example apparatus for sensing refractive index changes in an impurity-sensitive film. Similar approaches, including multiple film thicknesses, may be employed using other apparatus for sensing refractive index. For surface plasmon resonance, the upper cladding or second cladding is understood to be a material that is within a few evanescent decay lengths of a metallic film in which a portion of the surface plasmon propagates.

Various methods of data analysis may be used to estimate relative diffusion coefficients when applied to sets of curves such as those shown for different film thicknesses for a single analyte. For example, after determining the time required for each analyte and film-thickness combination to reach 20% of the change seen for the same analyte and the 1 µm thick film, those times can be plotted as a function of film thickness or the square root of film thickness for each type of analyte. If such a curve is steep (large time for 20% change) then the diffusion coefficient is relatively small, while a shallow curve of that time would indicate a large diffusion coefficient. The relative diffusion coefficients of potential analytes can be obtained from actual or simulated calibrations to inform which analyte is likely being sensed.

Another approach to analyzing the data for multiple sensing film thicknesses, is to define a new temporal function that is the ratio of two of the response curves (possibly offset), such as those shown in FIG. 2B, for two different film thicknesses for the same analyte. As an example, let $R_1(t)$ be the response for an analyte with a 1-micron thick film and $R_2(t)$ be the response for the same analyte in the same concentration with a 2-micron thick film. A normalized response ratio can be calculated as $y(t)=(R_1(t)+C)/(R_2(t)+C)$ where C is a constant used to shift the curves away from y values near zero to decrease the noise in the ratio at the expense of also decreasing the peak value of y. For the plots shown in FIG. 2C, C was chosen to be twice the absolute value of the maximum signal swing for a given analyte; thus C=8, 16 and 30 for the benzene, hexane and xylem data of FIG. 2B, respectively. The peak position, as may be parameterized in terms of the time of the peak or square-root of time of the peak, of such a normalized response ratio will be characteristic of the diffusion coefficient also known as the diffusivity, of a given analyte, relatively independent of the concentration of that analyte.

FIGS. 3A-3D show elevation, plan, and profile views of an exemplary hydrocarbon sensor 300 that includes hydrocarbon sensing regions 340a and 340b (collectively, hydrocarbon sensing regions 340) with different sensing film (upper cladding) thicknesses for detecting different types of hydrocarbons and/or hydrocarbon diffusion at different rates. Like the sensor 100 shown in FIG. 1, the sensor 300 shown in FIGS. 3A-3C includes an optical waveguide 310 formed of a core 301 between a first cladding 101 and coated upper cladding regions 201a and 201b (coated upper cladding regions 201) and exposed upper cladding regions 202a and 202b (collectively, exposed upper cladding regions 202). In this example, all four upper cladding regions 201 and 202 are made of the same material (e.g., a fluorinated polymer, such as Teflon AF), but one of the upper cladding regions (region 202b) is thinner than the other cladding regions. The upper cladding regions 201 and 202 may be formed from continuous material. The use of continuous material for the upper cladding may reduce optical scattering or reflections. The coated upper cladding regions 201 are also covered with respective hydrophilic barriers 501, such as a thin layer of metal or other relatively impermeable substance, and may be used as reference regions.

An advantage of using the same or similar materials or materials with similar refractive indices for both the coated upper cladding regions 201 and the exposed cladding regions 202 is that optical scattering is reduced. Configurations with abrupt changes in refractive index of any of the layers overlapping the optical mode, including the upper cladding, gives rise to scattering at those locations, and scattering can confound the measurement of changes in evanescent coupling of light to photodetectors as discussed below.

Figure 3A:
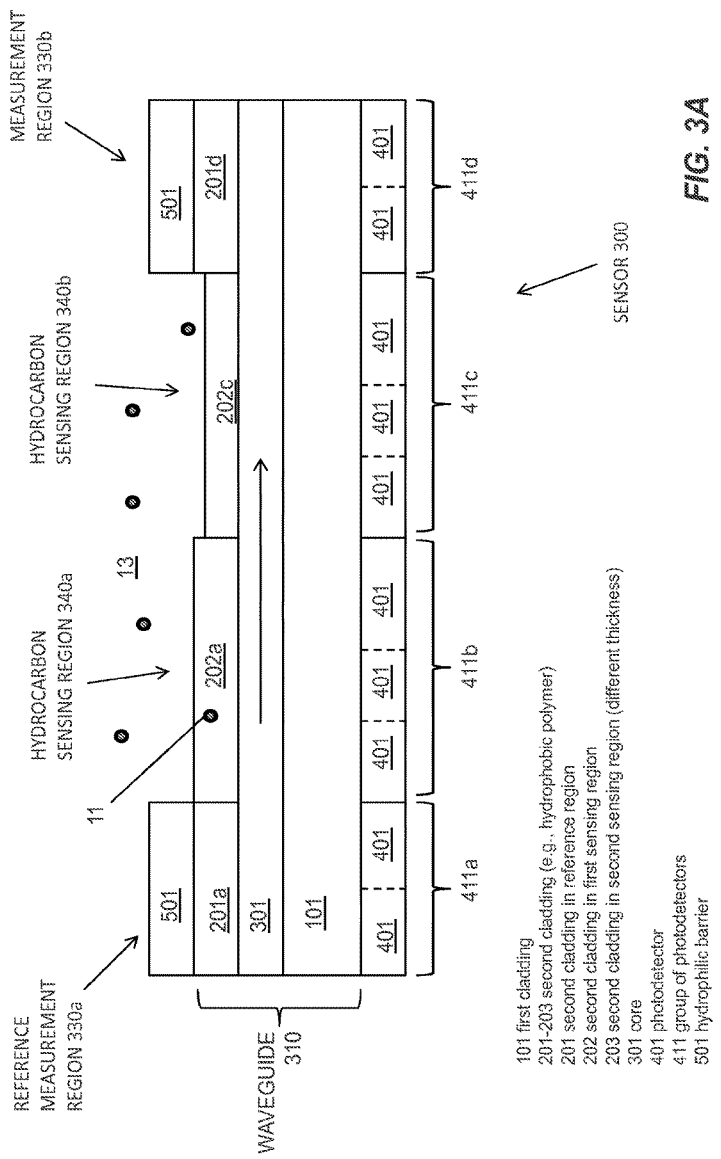
Figure 3B:
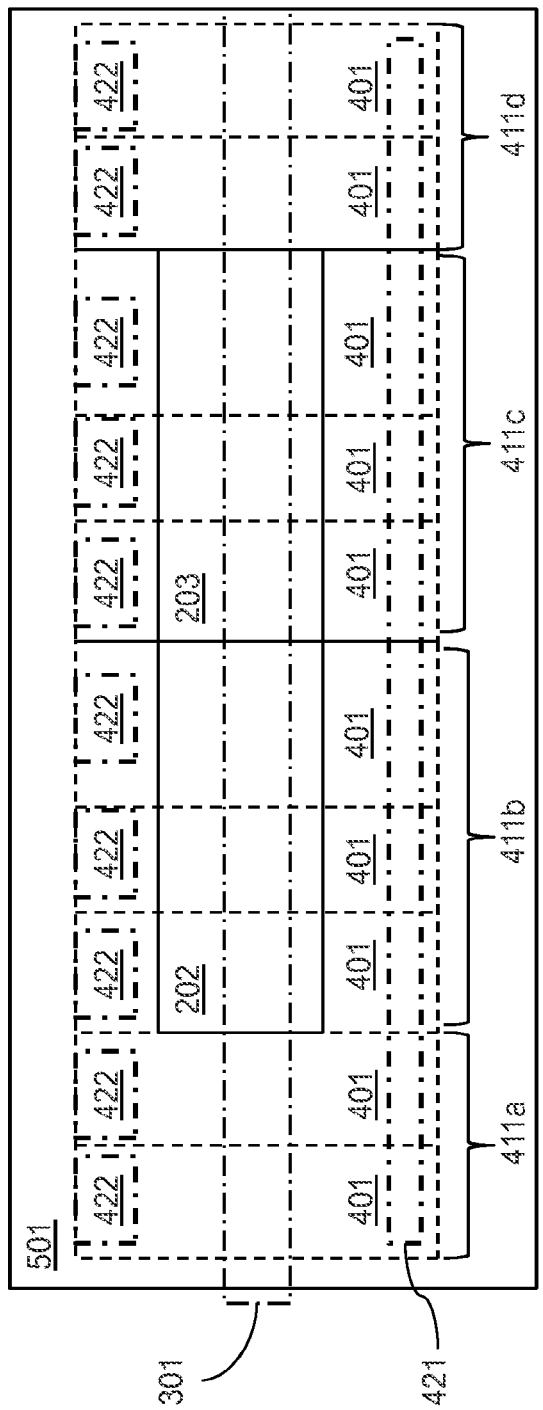

The sensor 300 also includes a plurality of photodetectors 411, each of which is electrically coupled to a common electrode 421 and to a respective independent electrode 422 as shown in FIG. 3B. Photodetectors may also use two electrodes that are independent of the electrodes of other photodetectors although this configuration is not shown in the figure. A dielectric insulator, such as $SiO_2$, insulates the common electrode 421 independent electrode 422 from other electrically conductive material in the sensor. The photodetectors 401 are arranged into photodetector groups 411a-411d (collectively, groups 411), each of which is opposite a respective coated upper cladding region 201 or exposed upper cladding region 202.

As shown in FIG. 3A, the exposed upper cladding regions 202a and 202b and photodetector groups 411b and 411c define the hydrocarbon sensing region 340a and 340b (collectively, sensing regions 340), respectively. In operation, a hydrocarbon-containing fluid 11, such as contaminated ground water, comes into contact with the exposed upper cladding regions 202, causing hydrocarbon molecules 13 in the fluid 11 to diffuse into the exposed upper cladding regions 202. Each hydrocarbon sensing region 340 has a respective diffusion constant, or diffusivity, that characterizes the speed with which the hydrocarbon molecules 13 diffuse far enough into the upper cladding 202 to produce a change in the upper cladding's refractive index measurable with the photodeteetor groups 411b and 411c. In this case, the second exposed upper cladding region 202b has a smaller diffusion time than the first exposed upper cladding region 202b because it is thinner than the first exposed upper cladding region 202b.

Different hydrocarbons (e.g., BTEX) may have different diffusivities and thus different diffusion times in the same material, making it possible to distinguish between different types of hydrocarbons 11 in the fluid 13. For example, benzene may diffuse into Teflon AF more quickly than xylene, but xylene may produce a greater shift in refractive index at a given concentration level. In such a case, the step response function, $f_{diff}(t)$, changes more rapidly for benzene than for xylene, but the absolute value of the equilibrium sensitivity, $S_{equil}$, is larger for xylene than for benzene. Because the sensor 300 has many different sensing regions 340, it may be able to make different measurements to disambiguate differences in diffusivity or diffusion time and varying amounts of refractive index change due to the presence of different hydrocarbons in the fluid 11.

In other examples, the fourth upper cladding regions may be formed of different materials, such as materials having different diffusitivities or different partition coefficients for a particular hydrocarbon or set of hydrocarbons, including but not limited to Teflon AF, trifluoroethylacrylate, hexylmethacrylate, chiorophenylacrylate, and combinations thereof (e.g., 82% hexylmethacrylate/18% chiorophenylacrylate).

Similarly, the coated upper cladding regions 201a and 201b and photodetector groups 411a and 411d define a first reference measurement region 330a and a second reference measurement region 330b, respectively. Diffusion barriers 501 on the coated upper cladding regions 201 inhibit the hydrocarbon from diffusing into the coated upper cladding regions 201. These barriers 501 can be hydrophilic and may have refractive indices approximately equal to those of the upper cladding regions 201. The barriers 501 make the coated upper cladding regions' diffusion times larger than those of the exposed upper cladding regions 202. (Alternatively, the upper cladding regions 201 can be left uncoated and made thicker than the exposed upper cladding regions 202 to provide longer diffusion times.)

Nevertheless, hydrocarbon molecules 13 can still diffuse into the coated upper cladding regions 201. For example, the hydrocarbon molecules 13 may diffuse laterally from the first exposed upper cladding region 202*a* into the first coated upper cladding region 201*a*.

Even with this diffusion, however, the reference measurement regions 330 can provide a reference measurement to account for fluctuations in optical power, temperature, etc. because they have higher diffusion times than the sensing regions 340. Differential measurements comparing the photocurrents flowing through photodetectors 401 in reference group 411*a* and photocurrents in sensing group 411*b* at various times following a change in hydrocarbon concentration may be used to improve sensing in the presence of lateral diffusion into coated upper cladding region 201*a*. Differential measurements may also be used to compare photocurrents generated from sensing photodetector groups 411*b* and 411*c* corresponding to different thickness of upper cladding regions 202*a* and 202*b*, respectively.

Figure 3E:
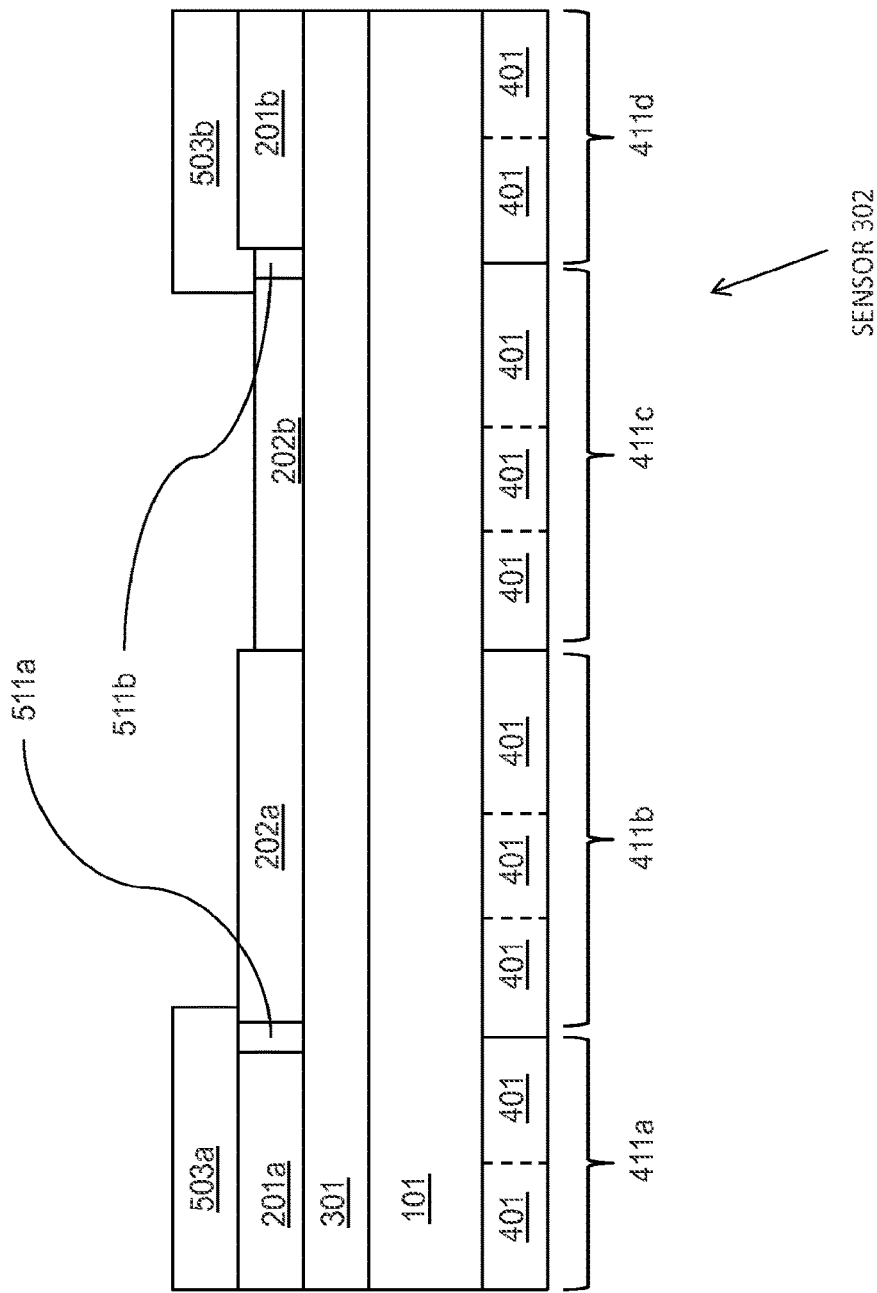
FIG. 3E is an elevation view of another exemplary sensor with hydrophilic barriers separating a hydrocarbon measurement region from adjacent reference measurement regions.

FIG. 3E shows an elevation view of a modified sensor 302 that includes a first lateral diffusion barrier 511*a* between upper cladding regions 201*a* and 202*a* and a second lateral diffusion barrier 511*b* between upper cladding regions 201*b* and 202*b*. The presence of the diffusion barriers 511 interrupts the continuity of the upper cladding regions 201 and 202 so that the upper cladding material is not continuous. This configuration may increase optical scattering or reflections at the interfaces of the diffusion barriers 511 and upper cladding regions if their refractive indices are substantially different. The modified sensor 302 also include extended diffusion barriers 503*a* and 503*b* that extend over the upper cladding regions 201*a* and 201*b*, respectively, and partially onto the upper cladding regions 202*a* and 202*b*, respectively. Together, the lateral diffusion barriers 511 and extended diffusion barriers 503 further increase the diffusion time constants, slow the diffusion step response function, $f_{diff}(t)$ or decrease the equilibrium sensitivity, $S_{equil}$, of the reference measurement regions by reducing the likelihood a hydrocarbon molecule diffusing in the upper cladding regions 201 in the reference measurement regions.

Surface Modifications for Enhanced Sensing if desired, the sensing film's surface can be enhanced to increase its affinity for BTEX or other nonpolar contaminants and/or to repel water and other polar molecules. For instance, the film surfaces can be made superhydrophobic by oxygen plasma etching the film for a period of time. Other methods include chemical treatment such as ones that alter surface charge or polarization susceptibility, or mechanical or chemical treatments that increase the film's surface roughness and lower its free energy. Experimental results show that plasma etching increases the film's uptake and hence sensitivity to BTEX contaminants, enabling enrichment concentration factors exceeding 100× in the film, which lowers (improves) the limit of detection of hydrocarbons.

Surface plasmon resonance measurements of the change in refractive index of plasma etched and non-plasma etched Teflon AF films exposed to a 30 ppm solution of benzene in water show the utility of rendering the sensing film superhydrophobic. The plasma etched films were etched in oxygen plasma in a reactive ion etching chamber at a power of 50 W and oxygen flow rate of 40 sccm for one minute. This particular etching process increased the water contact angle from 120° to 132°. Both the etching time and power can be adjusted in order to tune the hydrophobicity of the film. Typical etching times range from 30 seconds to 10 minutes, and typical powers range from 25 W to 200 W in a 30 cm diameter planar chamber, depending on the desired degree of surface roughness and hydrophobicity. Scaling of powers and times for different sizes of plasma processing chambers is understood by those skilled in the art of plasma processing. Surface roughness and texture affect hydrophobicity and can be altered by plasma etching.

The plasma etched and non-plasma films' refractive index changes were monitored using surface plasmon resonance measurements. In this case, FIG. 2D shows that the surface plasmon resonance peak shift, and hence analyte uptake, is enhanced by plasma etching by approximately 40% for benzene, as the field shift is 40% greater during the 5 minute sensing window.

Other methods for modifying the surface free energy and accordingly the hydrophilicity or hydrophobicity, including superhydrophilicity or superhydrophobicity, of polymer, hydrogel, hydrocarbon, metal, metal-oxide, insulator, or dielectric materials are known to those skilled in the art of solid-state materials surface modifications. And these methods may be practiced to alter the contact (wetting) angles or surface free energy of target analytes on both the sensing film and the barrier material to enhance the ratio of the partition coefficient of the sensing film to the partition coefficient of the barrier material with respect to the analyte concentration in the sample solution.

For examples, other methods for modifying the surface texture or chemistry of the sensing film include mechanically abrading the surface with an appropriate size grit of polishing material, hot embossing micro or nanostructure on the surface, or etching the surface through a shadow mask. Such a shadow mask may be continuous such as made by removing regions from a thin metal film, or the mask may be composed of multiple objects disposed on the surface of the sensing film prior to etching. For example, the film surface can be temporarily coated with micro or nanospheres prior to etching and with the nanospheres removed after etching. These and other described methods of surface modification may enhance the partition coefficient of the desired analyte solute into the film out of the sample solution.

Figure 3F:
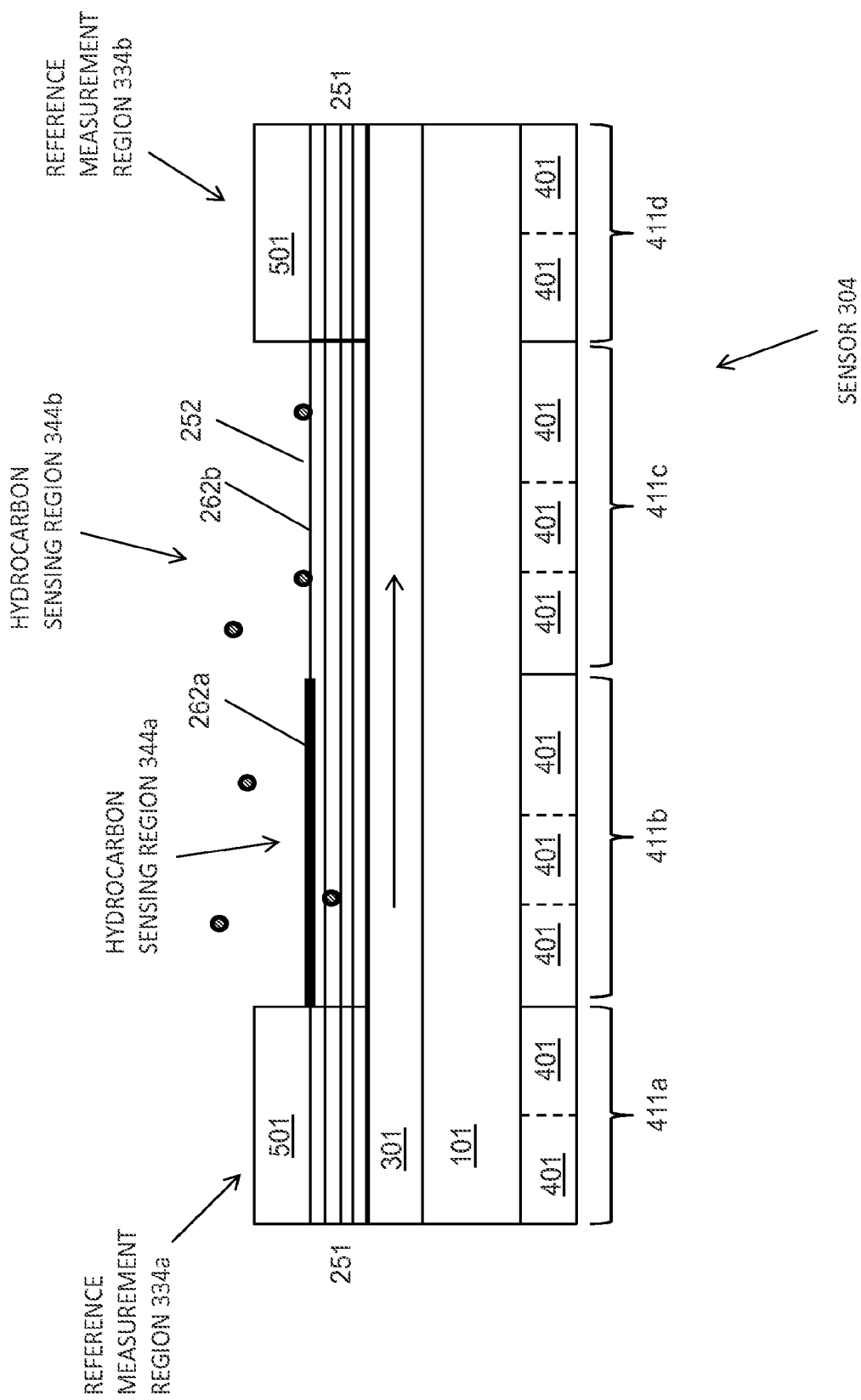
FIG. 3F is an elevation view of an exemplary sensor with a multi-layer upper cladding/sensing region.
Figure 7:
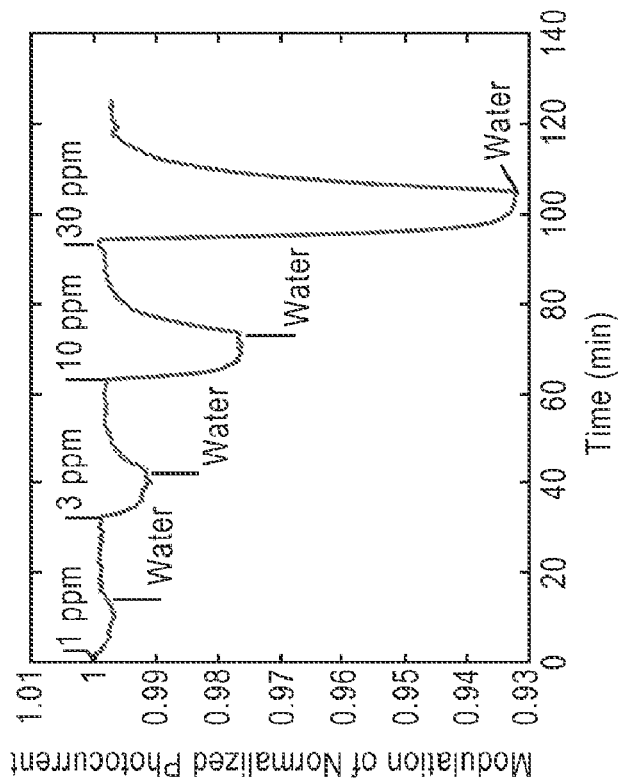
FIG. 7 is a plot of normalized photocurrent amplitude versus time as measured with an exemplary multi-analyte sensor during a xylene flow experiment.

FIG. 3F shows an optoelectronic hydrocarbon sensor 304 that includes an exposed upper cladding 252 with different surface treatments 262*a* and 262*b*. In this case, the upper cladding is formed of multiple films of fluorinated polymer. Diffusion barriers 501 inhibit hydrocarbon from diffusing into certain sections 251 of the upper cladding, forming reference measurement regions 334*a* and 334*b* with relatively long diffusion times as explained above. The rest of the upper cladding forms an exposed region 252, which may be patterned, etched, or otherwise treated to form different hydrocarbon sensing regions 344*a* and 334*b*. For instance, the first hydrocarbon sensing region 344*a* may include a plasma-etched region 262*a* of upper cladding, and the second hydrocarbon sensing region 344*b* may include an untreated region 262*b* of upper cladding. These surface treatments may increase or decrease the upper cladding's affinity for a particular hydrocarbon or group of hydrocarbons, which in turn may produce a variation in the equilibrium sensitivity or diffusion times for that hydrocarbon or group of hydrocarbons.

Scattering, Waveguide Design, and Sensor Performance

Optical waveguide sensor performance depends in part on the dimensions of the waveguide. If desired, the waveguide dimensions can be selected based on desired sensitivity, response time, dynamic range, and other sensor performance parameters. For example, the waveguide may be designed and fabricated based, at least in part, on the effect of scattering loss s because scattering can confound measurement of the evanescently coupled signal.

To see how scattering affects the signal, let P be the amount of optical power evanescently coupled into a given photodetector. And let the signal modulation M be the change in photodetector coupling from its initial value $P_o$ before solute diffusion to its final value $P_f$ after solute diffusion, such that $M=(1-P_f/P_o)$. Let $\alpha_o$ and $\alpha_f$ be the coefficients of evanescent power coupling before and after solute diffusion, respectively. Assuming a 300 µm (0.03 cm) photodetector length 1, the modulation at the first sensing detector for a scatter-free waveguide is given by:

$$M = 1 - \frac{1 - e^{-\alpha_f l}}{1 - e^{-\alpha_o l}}.$$

But the modulation when scattering is taken into account is given by:

$$M_s = 1 - \frac{(1 - e^{-\alpha_o l}) + (1 - e^{-sl})}{(1 - e^{-\alpha_f l}) + (1 - e^{-sl})}.$$

Here s is the scattering coefficient in units of inverse length and is elated to how rapidly optical power is scattered out of the waveguide and absorbed by the photodetector. The scattering coefficient is a function of multiple parameters including the dimensions of the waveguide and photodetectors, the roughness of the surfaces of the waveguide core, and the homogeneity of the refractive index of the waveguide materials. Note the impact of scattering on modulation: as s increases, modulation decreases, reducing signal to noise ratio and thus sensitivity.

Experimental measurements show that scattering losses can be significant. For example, scattering losses of 8±4 dB/cm were measured using calibrated camera measurements of scattered light attenuation on a series of test waveguides with a lower cladding thick enough (e.g., 3 µm) to render evanescent coupling negligible. The core and cladding thickness were chosen to reduce measured scattering losses. For one waveguide geometry, the first cladding 101 was 1.7 µm thick and the photodetector 401 was 25 µm wide and centered under the core 301. Assuming isotropic scattering in this example geometry, approximately 45.7% of scattered light is incident on the underlying photodetector ($\tan^{-1}(12.5/1.7)$). Of this 45.7%, about 60% is absorbed due to the angular averaged Fresnel reflectance. Thus, about 27.4% or s=2.2±0.3 dB/cm=0.5±0.07 cm$^{-1}$ was actually absorbed by sensing region photodetectors.

A two-dimensional, full-vector finite difference modesolver can be used to choose beneficial dimensions of the core (n=1.8) and lower cladding (n=1.46) subject to scattering losses. The photodetector coupling coefficient α (cm$^{-1}$) for both a pure Teflon AF upper cladding (n=1.31) and Teflon AF with diffused BTEX solutes (n=1.311) was computed for a wide range of core and lower cladding thicknesses with a 4 µm core width and silicon refractive index (n=3.83+0.014i). Simulations for widths of 2, 3, 4, 5, 6, 7 and 8 µm showed that a 4 µm wide core could support a single mode for waveguides far enough from cutoff so as to allow a sufficient amount of optical power to reach the sensing region. Other core widths are also possible, though they may exhibit higher sidewall scattering losses.

Fabrication of Optoelectronic Hydrocarbon Sensors

Exemplary optoelectronic hydrocarbon sensors (chips) can be fabricated using standard photolithography, wet etching, dry etching, metal deposition, metal liftoff and thin film deposition techniques. An exemplary fabrication process flow 400 is illustrated in FIGS. 4A-4H. This process should be taken as an example: other processes and variations on this process are also possible as readily appreciated by those of skill in the art. For brevity, photolithography and liftoff steps have been omitted from FIGS. 4A-4H, but Futurrex NR9-1500P photoresist can be used for wet etching. Futurrex NR71-3000P photoresist can be used for metal liftoff, and Shipley S1808 photoresist can be used for dry etching. While simulation results indicate that a 65 nm core and 2,000 nm lower cladding thickness would produce a higher sensitivity, a 70 nm core and 1,700 nm lower cladding thickness is selected, in order to render the device sensitivity less susceptible to small fluctuations (≤2 nm) in core thickness. The fabrication process 400 occurs as follows.

In FIG. 4A, an RCA cleaned, n-type <100>, 10$^{-5}$ ohm-cm prime grade wafer 402 is thermally oxidized at 1150° C. to form a 1,700 nm SiO$_2$ layer 404 using a dry-wet-dry oxidation scheme. After photolithography, the oxide is etched 1,600 nm with 6:1 buffered oxide etch (BOE), in order to from the waveguide's lower cladding as shown in FIG. 4B. In order to produce a high Schottky barrier, low dark current contacts for the integrated MSM photodetectors, Au is selected as the silicon contact metal. However, Au may adhere very poorly to oxide, so a thin layer 406 of Cr/Au is deposited on top of the oxide to serve as a metal adhesion layer for the Au/n—Si contacts as shown in FIG. 4C. After metal adhesion layer patterning, the remaining 100 nm of oxide is BOE etched to reveal the bare silicon as shown in FIG. 4D.

After photolithography, the Si native oxide layer is removed using a 3 second BOE dip followed by a dionized water rinse and N$_2$ drying. As shown in FIG. 4E, 35 nm of Au, 20 nm of Cr, and 75 um of Al (collectively denoted by reference numeral 408) are deposited at 0.1 nm/s to form the integrated MSM photodetector array. Au, Cr, and Al serve as contact, barrier and probing metals, respectively. After metal deposition, a core layer 410 of 70 nm SiN$_x$ (n=1.80) is deposited using plasma-enhanced chemical vapor deposition (PECVD) as shown in FIG. 4F. The 4 µm waveguide core is formed after photolithography by dry etching the SiN$_x$ 35 nm using a reactive ion etcher (RIE) flowing CF$_4$/O$_2$ (8%) at 50 sccm with a plasma power of 50 W as shown in FIG. 4F.

After waveguide core formation, a film of 412 Teflon AF 1600 is spin coated onto the chip as shown in FIG. 4G. As Teflon, like other upper claddings, does not readily adhere to silicon nitride, additional linker molecules may be useful. For example, the adherence of a hydrophobic film to a silicon-oxynitride or metal oxynitride waveguide core may be enhanced by using an adhesion promoter that firmly links a hydrophilic surface of a waveguide core to the adjacent surface of a hydrophobic thin film material that is used for the upper cladding. An example of such an adhesion promoter that may be appropriate for some films is Perfluorodecyltriethoxysilane. Other adhesion promoters may be provided by the manufacturers or vendors of the thin-film material such as adhesion promoters provided by DuPont for Teflon AF. In some cases, however, the adhesion promoter may interact with the target solute and/or other substances in the sample matrix. For example, some solutes reaching the adhesion promoter/thin-film interface may chemically alter or otherwise interfere with the binding between the adhesion promoter and the thin film upper cladding.

In this case, the adhesion promoter is dilute in methanol to a concentration of 5%, then spin coated onto the chip at 1000 RPM. The coated substrate is baked on a hot plate at 110° C. for ten minutes before the Teflon film is spin coated onto the chip 4 times at 800 RPM. Between each spin coat, the film is cured in an oven at 300= C. for one hour with a 25° C./min ramp time. After curing, the film is etched in an RIE for 5 seconds in oxygen plasma at a flow rate of 50 sccm and a power of 50 W. The plasma etch is necessary to ensure that the layers of Teflon adhere to each other. This process yields a Teflon film with a thickness of about 6 μm as measured by white light spectrometry. After Teflon patterning, the film is once again plasma etched prior to the next photolithography step, in order to ensure photoresist adhesion to the Teflon.

After photolithography, 200 nm of aluminum 414 is deposited to form a BTEX permeable blocking layer for the reference detector as shown in FIG. 4H. After this step, the sensing region detectors are directly exposed to the analyte solution and the reference measurement regions are shielded from the analyte solution. This is done to prevent other regions of the chip from absorbing solutes from the sample volume. After the metal reference region patterning step, the remaining Teflon in the sensing region is oxygen plasma etched to a depth of 1200 nm. Teflon serves the dual purpose of sensing film and insulating layer. Plasma etching has the added advantage of oxidizing the aluminum, forming a hydrophilic metal oxide capping layer. In the next step (not shown), the remaining Teflon in the probe pad region of the chip is removed through oxygen plasma etching to permit electrical contact with the chip. The waveguide facet is then polished so that light can be end-fire coupled into the waveguide.

FIG. 5A is an optical microscope image of an optoelectronic hydrocarbon sensor produced using the process 400 of FIGS. 4A-4H. The optical microscope image shows the chip's reference and sensing region with corresponding 300 μm long reference and sensing photodetectors. The waveguide core and lower cladding are seen in the sensing region near the top of the image and continue into the reference region, but cannot be seen below the opaque aluminum blocking layer. As photogenerated electronic carriers can diffuse laterally, a 100 μm sweep detector separates the reference detector from the first sensing detector.

FIG. 5B is a scanning electron microscope (SEM) image of an optoelectronic hydrocarbon sensor taken before Teflon AF and reference region patterning (FIG. 4G). The reference detector, sweep detector, and first sensing detector are labeled in the image along with the shared bias contact. The sweep detector is used to prevent sensing and reference electrodes from collecting photocurrent front the reference and sensing regions, respectively. For n-type Si, the individual photodetectors are reverse biased at 2 V, by applying a 5 V bias to the shared contact and a 3 V bias to the individual detectors. The apparent overlap of separate metal contacts at the narrow ends of the electrodes is an artifact resulting from the 45 degree tilt at which the SEM image was acquired.

Figure 6:
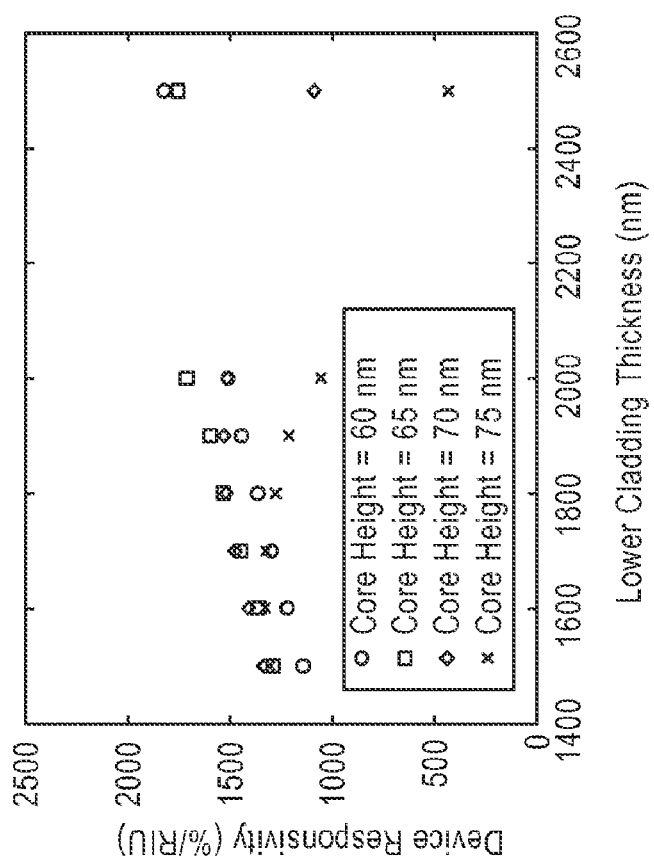
FIG. 6 is a plot of device sensitivity as a function of waveguide core and lower cladding dimensions.

FIG. 6 is a plot of device sensitivity as a function of waveguide core and lower cladding dimensions based on computer simulations and calculations. (Companies that offer software for computing optical mode profiles include RSoft Design Group, VPI systems and Optiwave Systems. The software used for mode profile simulations that were used for FIG. 6 was obtained from the University of Maryland.) The optical mode profiles can be computed from given inputs of waveguide component dimensions including core and cladding thicknesses and the lateral width and profile of the core as fully or partially etched, as well as the refractive index of these layers, and the optical wavelength. The absorption properties of the photodetector layer also serve as an input and can be represented in the simulations as an imaginary component of a complex refractive index, such as that for silicon or other semiconductors at photon energies greater than their bandgap energy.

Multiple simulations of otherwise identical structures can be performed with small variations in the refractive index of the upper cladding, which is potentially a hydrophobic polymer, to represent the effect of changes in impurity, such as aromatic hydrocarbon, concentration. For example, the refractive index of Teflon AF with two different concentrations of benzene might he assumed to be 1.312 and 1.313, and a mode profile and corresponding complex effective index can be calculated for each refractive index, where the imaginary part of the mode's effective index represents the coupling loss of the mode to the photodetector when no other absorbing materials are included in the simulation. The difference in the absorption coefficient for the mode with the two different refractive indices can be normalized to the absorption coefficient of either one to determine an approximate fractional or percentage change in the coupling loss and hence approximate fractional or percentage change in the photocurrent. Dividing the percentage change in the photocurrent, which is approximately equal to the percentage change in the photodetector coupling loss, by the change in refractive index, which is 0.001 refractive index units (RIU) for this example, gives the device responsivity or sensitivity plotted on the vertical axis of FIG. 6. FIG. 6 shows that for the smaller core thicknesses (heights), the normalized sensitivity increases with lower cladding thickness, i.e., the distance between the core and photodetector. However, for larger core thicknesses, this trend changes for some particular lower cladding thickness where the sensitivity is maximum. For example, a core thickness of 70 nm results in a maximum sensitivity of about 1500%/RIU achieved with a lower cladding thickness of 1900 nm.

In addition to considering the desired sensitivity when designing core and cladding thickness, the designer should also consider the amount of coupling loss, $\alpha$, and thus the rate of power decline along the waveguide as this may limit the useable length of waveguide and hence the number of different sensing regions along the waveguide. Layer thickness may also be selected based at least in part on the desired device sensitivity, coupling loss, dynamic range and other sensor parameters.

Measurements with Optoelectronic Hydrocarbon Sensors

FIGS. 7-13 are plots of experimental measurements made with exemplary optoelectronic hydrocarbon sensors. For each of the example experiments described below about 1 mW of optical power from a 660 nm laser diode was fiber-coupled into the sensor waveguide. To minimize fluctuations in coupled light intensity, the 4/125 μm fiber was epoxied to the waveguide facet. For fluid handling, a custom-machined flow cell with a volume of 200 μL was clamped onto the chip and sealed with a 1/16" diameter O-ring. Smaller dimensions and volumes of flow cells could be achieved with microfabrication techniques. Sample solutions were manually injected into the fluidic chamber via small diameter tubing using a syringe. An probe card was used to contact the sensor chip's readout pads for photocurrent measurement. Electrical contact to the readout pads could also be achieved with wire-bonding, bump bonding or other similar electronic packaging techniques.

Data Acquisition System

Photocurrents on the chip's photodetectors were measured using a custom data acquisition system, which permitted near simultaneous photocurrent measurement on all photodetectors at a sampling rate of 2 kHz. The system included a battery-powered, single-supply, 8-channel transimpedance amplifier (TIA) connected to an 8-channel analog-to-digital converter (ADC), which then interfaced with a computer running Labview for automated data acquisition. The TIA included a gain stage, which ranged from 0.4 V/μA to 2 V/μA depending on detector position along the waveguide. Photodetectors near the optical fiber or optical source have higher photocurrents and thus may be coupled to lower gain TIAs. The gain stage was followed by a two-pole Butterworth 6 Hz low pass filter to reduce noise. To reduce drift and noise, "zero drift" op amps (LTC 1050, Linear Technology) were used for both amplifier stages.

To collect generated carriers, a 2V bias is supplied across the metal-semiconductor-metal contacts. Other values of bias voltage may he used on metal-semiconductor-metal or other symmetric photodetectors. Bias voltage should be chosen to provide sufficient photocurrents while avoiding noisy operation or excessive sensitivity of the photocurrent to the exact bias voltage. Other possible photodetectors, including asymmetric ones such as p-n or p-i-n photodetectors may be used with or without bias voltage as they contain built-in electric fields causing the generated carriers to move towards electrodes even in the absence of applied bias voltages.

Signal Processing and Conversion to Normalized Photocurrent

Prior to each experiment, the dark current on each detector is recorded and averaged over a period of 8 seconds to give $I_{dark,i}$ for each detector. The dark current on each detector is then subtracted from the measured current $I_{meas,i}$ when light is coupled into the waveguide, to give the photocurrent on the detector $i_{th}$ detector $I_{det,i}=I_{meas,i}-I_{dark,i}$. The dark current on each detector was approximately 400 pA, corresponding to a Schottky barrier height of 0.7 eV.

To increase the signal-to-noise ratio (SNR), photocurrent measurements on all channels are averaged over 8 seconds (16,000 samples per detector). After averaging, the raw photocurrent on the $i_{th}$ sensing photodetector $I_{det,i}$ is normalized by dividing by the reference region photocurrent $I_{ref}$ such that $I_{norm,i}=I_{det,i}/I_{ref}$. The on-chip photocurrent reference region is used to correct for changes in coupled light intensity and temperature-related drift, in order to better resolve changes in photocurrent solely caused by solute diffusion into the chip's upper cladding sensing film. After reference photocurrent normalization, all photocurrents are divided by the maximum value on the first sensing detector ($I_{norm,i}$) so that all normalized photocurrent values are between 0 and 1.

BTEX Sensing Experiments

A series of experiments was conducted to characterize the sensing performance of six nominally identical chips (labelled B1, B2, B3, X1, T1 and E1) fabricated on the same wafer. Experiments were designed, in order to determine a limit of detection for BTEX solutes, sensor reusability, sensor repeatability, and interference from other contaminants and temperature fluctuations.

Temporal Resolution of Solute Diffusion

For benzene, toluene and xylene sensing experiments, three separate chips (X1, T1, and B1) were used, respectively. To better mimic true environmental sampling conditions, test solutions were prepared using water drawn from Horsetooth Reservoir in Fort Collins, Colo. (An initial experiment on chip X1 showed no measureable change in photocurrent when deionized (DI) water was injected into the flow cell followed b reservoir water, implying that any potential contamination in the reservoir was below the limit of detection of the system). Solutions of high-purity benzene, toluene, and a mixture of the three xylene isomers were prepared at concentrations of 1 ppm, 3 ppm, 10 ppm, and 30 ppm in reservoir water.

For each experiment, reservoir water is injected into the flow cell and data is recorded for two minutes in order to establish a baseline. Then the 1 ppm solution is injected and data is acquired for 15 minutes followed reservoir water injection and another 15 minute measurement period. This procedure is then repeated for the 3, 10 and 30 ppm concentrations. A time trace of the normalized photocurrent on sensing detector #1 is displayed for xylene in FIG. 7. As expected, the photocurrent decreases as xylene diffuses into the film, increasing concentrations near the waveguide core. Subsequently, when xylene-free water flows into the channel, the xylene diffuses out of the film and the modulation signal returns to the baseline, indicating that the chip is reusable upon exposing the sensing region to clean water for a sufficient period of time.

Effect of Solute Diffusion on Mode Propagation

Figure 8:
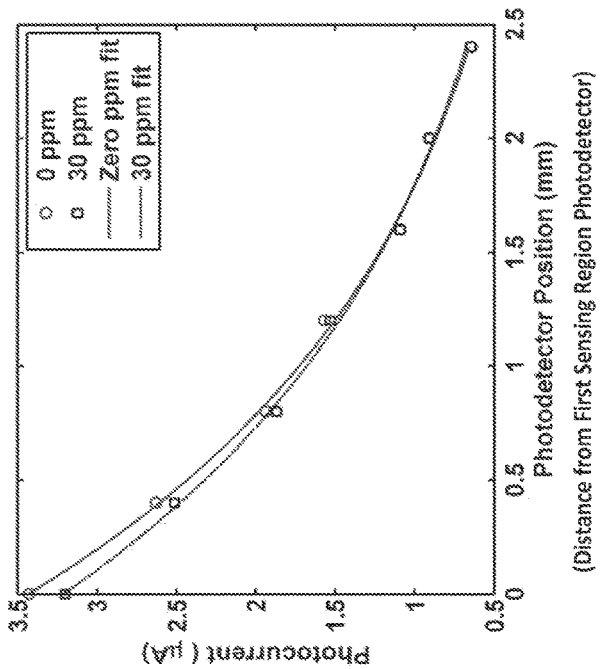
FIG. 8 is a plot of photocurrent amplitude versus photodetector position as measured with an exemplary multi-analyte sensor detecting xylene at a concentration of 30 ppm.

In order to investigate how solute diffusion affects light propagation and evanescent coupling along the length of the waveguide, a total of seven sensing detectors were included on the chip. FIG. 8 is a plot of the measured photocurrent on each sensing detector for water and a water sample contaminated with 30 ppm of xylene, which was allowed to equilibrate for 15 minutes. The data from the chip's seven detectors are plotted versus position along the waveguide from the first sensing detector. The raw photocurrent data is presented to demonstrate the effect of solute diffusion on evanescent coupling. (In order to resolve changes in evanescent photodetector coupling with higher precision, the reference photodetector can be used to compute a dimensionless normalized photocurrent.)

As a result of xylene diffusion into the sensing region, the calculated evanescent coupling strength decreases from $\alpha_{water}=6.89$ cm$^{-1}$ to $\alpha_{xylene}=6.49$ cm$^{-1}$. The greatest change in modulation is found on the first sensing photodetector (M=8.4%), whereas the modulation on the seventh photodetector is about M=1.4%. Without being limited by any particular theory, it appears that the decrease in modulation results from two competing effects. Due to the increased upper cladding index in the upstream sensing region, more optical power reaches the seventh photodetector. As a result, the decrease in localized photodetector coupling is counteracted by the increased optical power entering the seventh sensing region. Thus, in practice, the sensor can detect contaminants using the reference detector and any one of the sensing photodetector.

Response Linearity

Figure 9:
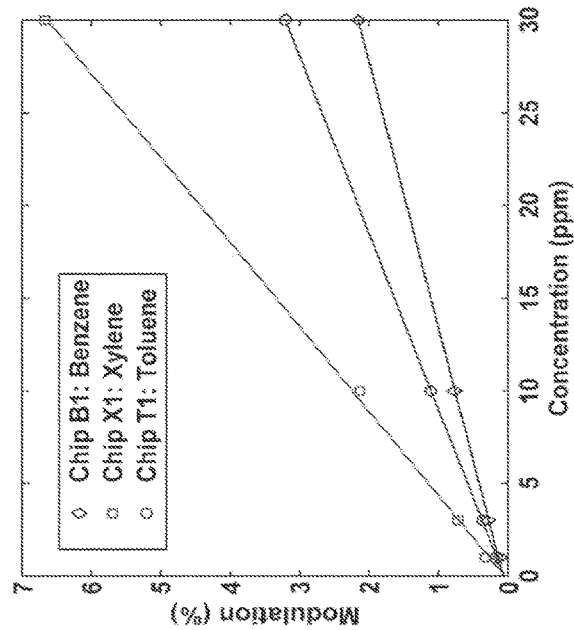
FIG. 9 is a plot of the modulation response of different sensors (Chips B1, X1 and T1) to benzene, xylene, and toluene as a function of hydrocarbon concentration.
Figures 10, 11:
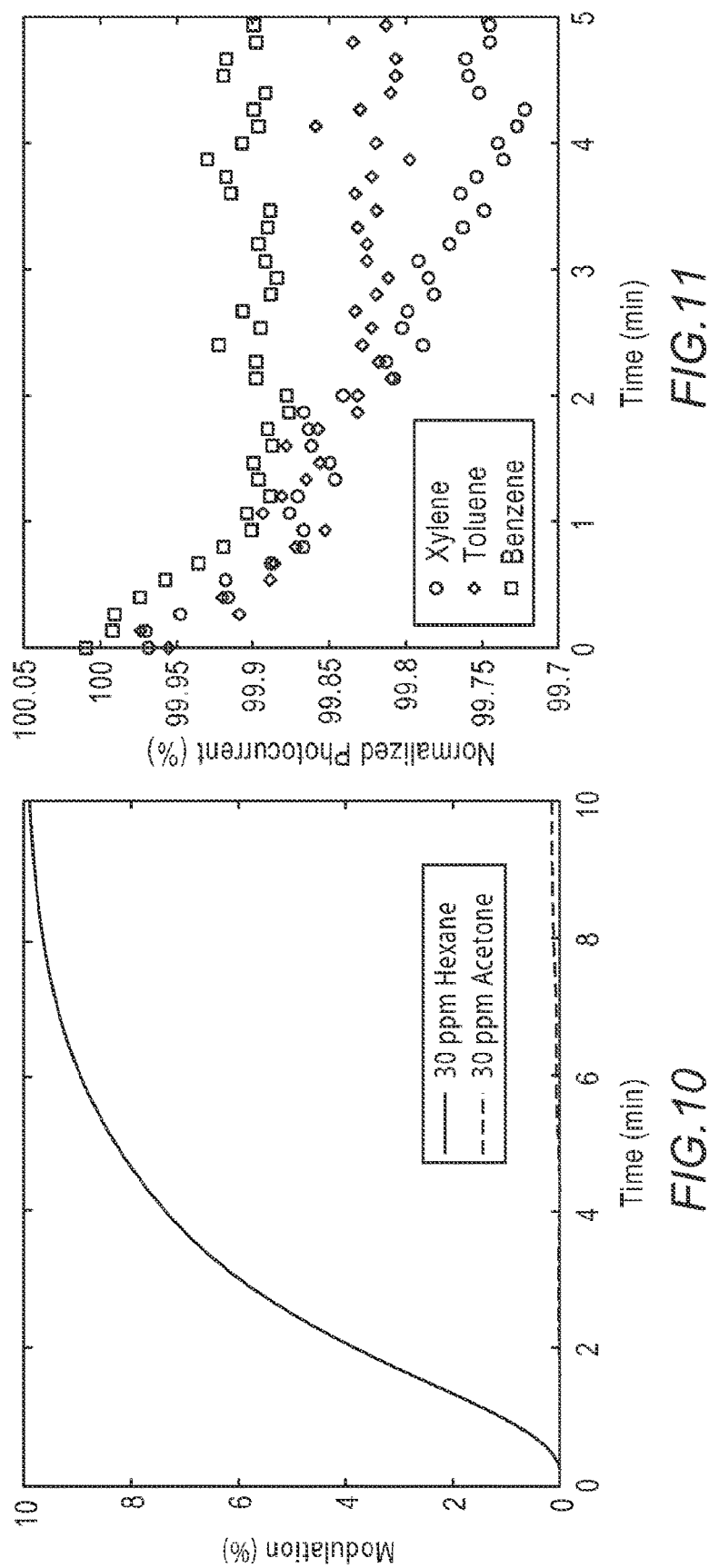
FIG. 10 is a plot of the modulation response of a sensor exposed to 30 ppm solutions of acetone (lower trace) and hexane (upper trace) as a function of time.
FIG. 11 is a plot of the normalized photocurrent versus time for a sensor exposed to 1 ppm solutions of benzene (squares), toluene (diamonds), and xylene (circles).

FIG. 9 shows the responses of chips X1, T1, and B 1 to 1, 3, 10 and 30 ppm concentrations of xylene (squares), toluene (circles), and benzene (diamonds), respectively, as a function of concentration. Results are for a 15 minute equilibration time period at each concentration. The traces represent linear curve fits for the sensors' responses to BTEX solutes, as indicated by R-square values exceeding 0.99 for all lines of best fit.

Device Repeatability

To evaluate measurement repeatability across multiple chips, the benzene flow experiment used for chip B1 was repeated on chips B2 and B3 at concentrations of 1, 3 10 and 30 ppm. The average standard deviation in sensitivity across the four concentrations tested is 18.3% for a 15 minute exposure period. Without being bound by any particular theory, the de-viation in sensitivity between chips B1, B2 and B3 is likely caused by differences in scattering loss among the chips. Based on the scattering model presented above, a waveguide with a scattering loss of 4 dB/cm could provide a sensitivity of 1,520%/RIU vs. 1.398%/RIU for a loss of 12 dB/cm, an 8% difference. While care was taken to prepare capped solutions identically followed by sonication before sample extraction with a syringe, it is possible that the deviation in response could have also resulted from concentration differences in the solution being sampled.

Effect of Temperature Fluctuations

For laboratory experiments, the sample solutions were allowed to equilibrate to room temperature in a controlled temperature environment. For field measurements, it would likely be more difficult to control the temperature of both the pure water reference solution used for establishing a baseline reading and the sample undergoing analysis. Additionally, if the sensor chip were used for long-term monitoring, the ambient sample medium would likely undergo relatively large temperature fluctuations. In order to evaluate the effect of temperature on device performance, the following experiment was conducted on chip E1. First a room temperature water sample (22° C.) was injected in the flow cell. Then a sample of chilled ice water was injected into the sample flow cell, yielding a near-instantaneous temperature deviation of ~22° C. The maximum deviation in the normalized photocurrent was found to 0.44%, corresponding to temperature stability of 0.02%/° C. The use of on-chip or off-chip temperature sensors with optional temperature controlling devices such as thermoelectric coolers (TECs) or on-chip or off-chip resistive heaters could be used to compensate for or reduce temperature dependent changes in normalized photocurrent.

Effect of Interference from Other Matrix Contaminants

A given water sample may contain a variety of ionic and nonpolar contaminants, in addition to BTEX contaminants. Thus, it is important to investigate the effect of other potential sample matrix contaminants. Solute uptake by Teflon films has been shown to exhibit a strong dependence on the solute's octanol-water partition coefficient, $P_{ow}$. Thus, 30 ppm of hexane ($\log(P_{ow})$=4.0) and 30 ppm of acetone ($\log(P_{ow})$=−0.24) were selected as test solutions to span a large range of octanol-water coefficients. To evaluate the effect of ionic contaminants, a 4% NaCl solution, used to mimic ocean water was used.

Chip E1, which had previously been use for temperature fluctuation measurements, was also used to characterize interference effects from other matrix contaminants. First, a water baseline reading was taken. Then the 4% saline sample was injected into the flow cell and allowed to equilibrate for 10 minutes followed by a 15 minute water rinse. Then the acetone solution was injected, followed by a 15 minute water rinse. Lastly, the hexane solution was injected into the channel. The rinse step was included to avoid cross-contamination of the interfering solutes being analyzed and bring the film back to baseline. The data showed no measurable change for the 4% NaCl solution. The data for the hexane solution and the acetone solution are plotted in FIG. 10, where t=0 corresponds to the time when each solute is injected into the flow cell. The normalized photocurrent shift is 9.96% for hexane, but only 0.16% for acetone, consistent with the partitioning behavior of these solutes into Teflon AF.

Experimental Device Sensitivity and Limit of Detection

The sensor sensitivity, $dM_s/dn$ is given units of %/refractive index unit (RIU) and parameterizes the fractional change in optical power coupled to a photo detector for a given change in refractive index. Generally speaking, sensitivity increases monotonically with lower cladding thickness up to a certain thickness and then begins to fall of rapidly as the lower cladding thickness increases further. Without being bound by any particular theory, it appears that this inflection point is caused by the fixed scattered light intensity overwhelming the evanescently coupled signal for larger lower cladding values because the magnitude of evanescently coupled power falls off exponentially as the lower cladding thickness increases.

If desired, the sensor's sensitivity can be engineered by selecting the waveguide dimensions appropriately. For instance, a sensitivity of approximately 1700%/RIU is found for a core thickness of 65 nm and a lower cladding thickness of 2,000 nm, where $\alpha_o$=3.0 cm$^{-1}$ for n=1.31. This sensitivity value is comparable to intensity-based surface plasmon resonance systems.

Experimentally, the device sensitivity is 0.22%/ppm, 0.11%/ppm and 0.07%/ppm for xylene toluene and benzene, respectively based on the lines of best fit in FIG. 9. In order to calculate the chip's limit of detection (LOD) for a five minute measurement time window, which is sufficient to allow nearly full equilibration for all BTEX solutes with the 1200 mm thick Teflon AF layer, the data for the 1 ppm concentration tested (FIG. 11) were analyzed in the following manner. First, the change in normalized photocurrent $\Delta M$ is calculated from t=0 to the average value for last five data points the sample window. Then the standard deviation $\sigma$ in the normalized photocurrent is computed for last five data points in the sample window (t=4.46 to 5 minutes) Per IUPAC definition, the limit of detection is the given by LOD=(3$\sigma$/$\Delta M$)×(1 ppm) and is found to be 359 ppb, 249 ppb, and 103 ppb for benzene, toluene and xylene, respectively.

Identifying Contaminants from Their Diffusion Coefficients

At least one exemplary hydrocarbon sensor can identify the type of contaminant based on a measurement of the contaminant's diffusion coefficient. Because different contaminant molecules have different diffusion coefficients in a given sensing film and different refractive indices, they may produce different changes in the sensing film's refractive index. For example, they may change the sensing film's refractive index at different rates or by different amounts for a given concentration. Measurement of the contaminant's diffusion coefficient using a diffusion-model based extraction algorithm enables identification of the particular contaminant. Additionally, the diffusion theory model permits rapid determination of the solute's concentration in the liquid sensing medium.

The diffusion coefficient, and hence diffusion of the solute front inside the film, is dependent on the solute type. For instance, acetone has a much high diffusion coefficient than benzene, whereas benzene has a lower diffusion coefficient than n-hexane. The different diffusion coefficients can be used for analyte identification purposes, as they result in distinct diffusion curve shapes approximately independent of concentration for low concentrations as shown in the FIG. 2A, where the surface plasmon resonance peak shift due to 10 ppm concentrations of benzene, toluene, xylenes, and n-hexane has been simulated, in addition to a 1000 ppm concentration of acetone for a 10-micron thick film. By incorporating a structure with multiple film thicknesses, analyte identification is enhanced using standard curve fitting techniques and inclusion of a reference diffusion curve library, which may be generated either through calibration experiments on single analyte test solutions or from prior knowledge of the solutes diffusion coefficient in the chosen sensing film.

By employing a diffusion theory model, it is possible to identify primary individual BTEX solutes based on extraction of their diffusion coefficients.

The diffusion of BTEX solutes in Teflon AF films has previously been shown to be obey the solution to the diffusion equation whose solution is shown as Equation 1. Here K is the solute's partition coefficient into the film; $z_{film}$ is the film thickness, $C_o$ is the solute's concentration in the contaminated water sample and D is the solute's diffusion coefficient or diffusivity.

$$C(z, t) = KC_o - \frac{4KC_o}{\pi} \sum_{n=0}^{\infty} \frac{(-1)^n}{2n+1} \exp\left\{\frac{-D(2n+1)^2\pi^2 t}{4z_{film}^2}\right\} \cos\left\{\frac{(2n+1)\pi z}{2z_{film}}\right\}. \quad (\text{Eq. 1})$$

While curve fitting can be used to extract a solute's diffusion coefficient from the measured data, analysis shows that while the magnitude of the response (signal modulation) depends on both $C_o$ and K, the shape of the diffusion curve and hence, the time to reach a particular fraction of the equilibrium change is only dependent on D within the linearity assumptions implicit in the diffusion equation. From the time trace data shown for 30 ppm concentrations of benzene, toluene and xylene in FIG. 12, it is evident that the rate at which each contaminant approaches equilibrium in the film varies. Reading from the plot, the time to reach 99% of equilibrium is approximately 128 s, 184 s and 344 s for benzene, toluene and xylene respectively.

From Eq. 1, the time for a solute with diffusion coefficient D to reach within 1% of equilibrium for a 1200 nm thick film is plotted in FIG. 13. For the measured 99% of equilibrium times, the diffusion coefficients are estimated to be $2.22 \times 10^{-10}$ cm$^2$/s, $1.54 \times 10^{-10}$ cm$^2$/s, and $0.81 \times 10^{31}$ $^{10}$ cm$^2$/s for benzene, toluene and xylene, respectively. These values are comparable (to within 10%) of previously published values. For field measurements, this technique would permit a lookup-table approach for discriminating contaminants based on the measured diffusion coefficient. Ambiguities created by different contaminants having similar diffusion coefficients in a sensing material could be resolved by employing multiple impurity-sensitive sensing materials so that contaminants of interest would have resolvably different diffusion coefficients in at least one of the materials.

Figure 14:
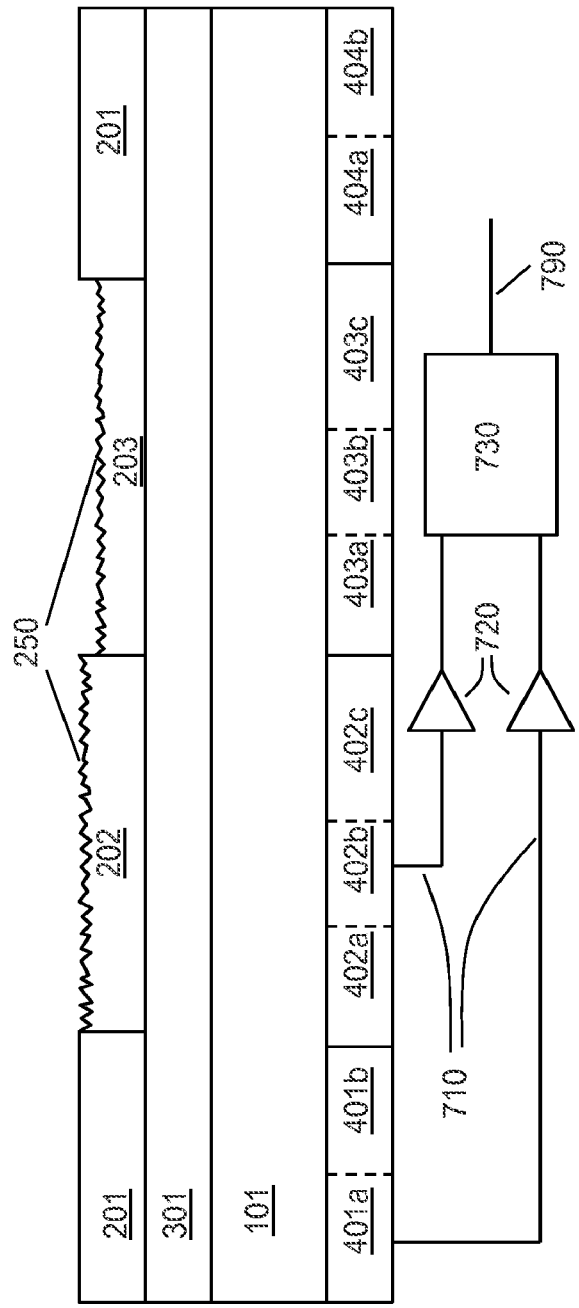
FIG. 14 is an elevation view of an exemplary sensor with textured regions to alter hydrophobicity and showing signal connections from photodetectors to a processor.

FIG. 14 is an elevation view of an exemplary sensor similar to the one shown in FIG. 3A but with textured surfaces 250 to alter the hydrophobicity of sensing regions 202 and 203. In the example shown, the reference regions 201 and 204 are not as textured as the sensing regions 202 and 203. Thus the reference regions 201 and 204 may have lower hydrophobicity, lower partition coefficients, and/or lower responses to hydrocarbons than the sensing regions 202 and 203. Sensing region 202 may have a different amount or type of texture than thinner sensing region 203 and thus exhibit a different hydrophobicity. The amount of surface texture can be defined in terms of the RMS surface roughness, the distribution of angles on the surface, other measures of surface texture and roughness or a combination of these measures. Surface texture with re-entrant profiles or equivalently overhangs or acute angle corners may be used. Surface texture with fractal or multi-scale geometries may be used. Other techniques may be used to alter hydrophobicity including chemical treatments, coatings, or porosity alone or in combination with surface texture.

FIG. 14 also illustrates the electrical connection 710 of a sensing region photodetector 402b and a reference region photodetector 401a to amplifiers 720 and subsequently to a processor 730. The processor performs analog or digital processing of the amplified photodetector signals to produce an output 790 which may be more readily correlated to the hydrocarbon concentration or change in concentration than the individual signals from the photodetectors (401 through 404). The processor 730 may receive multiple amplified or unamplified signals from multiple photodetectors in one or more reference and one or more sensing regions. The figure shows inputs from only two detectors for simplicity of illustration. The output of the processor may be an electronic signal or a numeric representation. The processor 730 may contain one or more analog-to-digital convertors, multiplexing switches, analog or digital filters, phase-locked loops, lock-in amplifiers, digital signal processors, microcontrollers, or other programmable units. The processor may compute the ratio, differences, averages, or other functions of the photocurrents or changes in photocurrents of the photodetectors 401 through 404. The amplifiers 720 may be voltage or transimpedance amplifiers. The electronic connections 710 may be wires, on-chip metallization, printed circuit board traces or other known forms for electrical interconnection of electronic components. The amplifiers 720 may be distinct from the processor 730 as shown in the figure or they may be incorporated into the processor.

Figure 15:
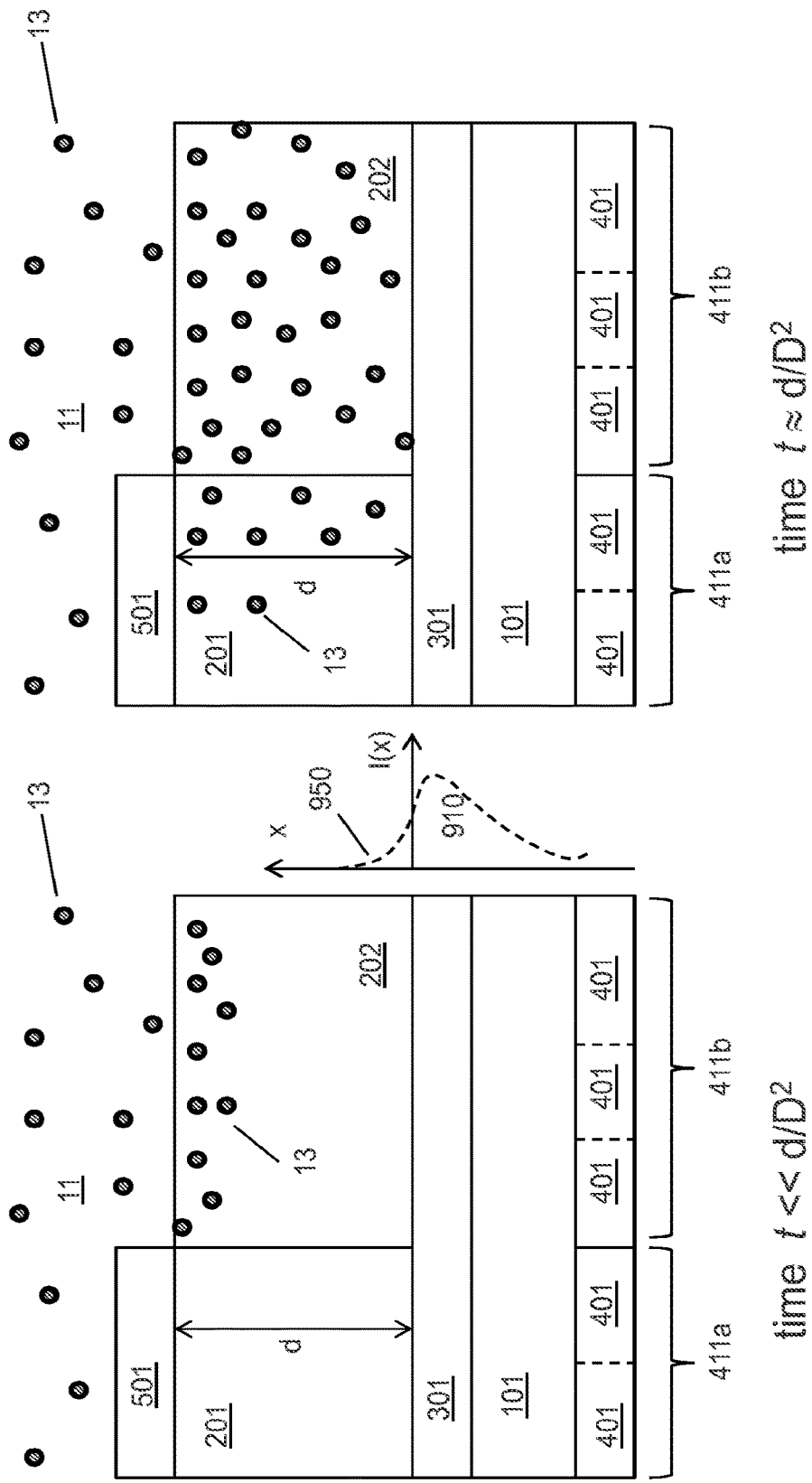
FIGS. 15A and 15B show the diffusion of impurities into sensing and reference regions at two different times.

FIG. 15A shows a solution 11 containing impurities 13 during initial diffusion of the impurities 13 into the exposed upper cladding region 202 at a time much shorter than the time required to diffuse through the thickness, d, of the upper cladding 202. FIG. 15B shows a later time when the impurities 13 have diffused toward the waveguide in the exposed upper cladding region 202 as well as laterally into the coated upper cladding region 201. Also shown in FIG. 15A is the optical intensity profile 910, I(x) as a function of position, x, in the upper cladding. The evanescent tail of the optical intensity profile 950, primarily overlaps the portion of the upper cladding 201 and 202 that is proximate to the waveguide core 301.

The concentration of impurities just inside the exposed upper cladding region 202 adjacent to the solution 11 is greater than the concentration of impurities in the solution 11 adjacent to the exposed upper cladding 202 in this example, illustrating the effect of a partition coefficient that is greater than one.

Figure 16:
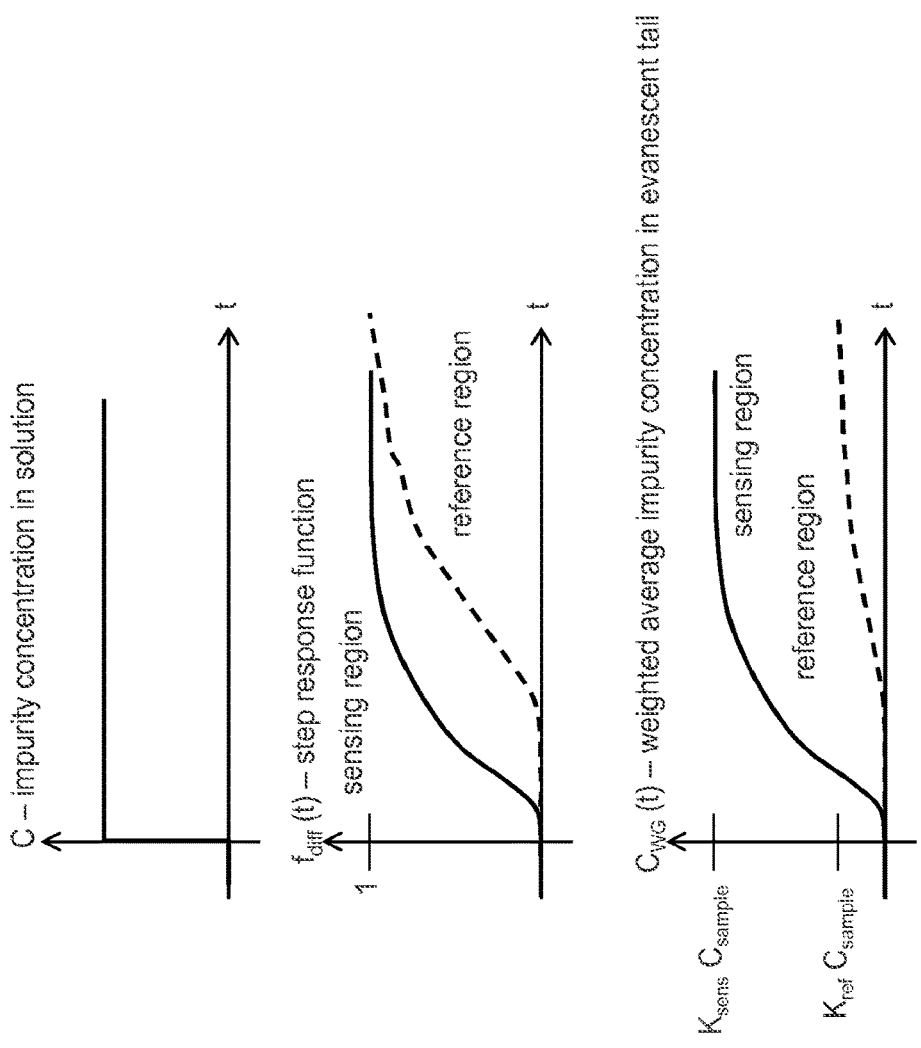
FIG. 16 illustrates exemplary diffusion step response functions and waveguide sensed impurity concentrations after a sudden change in sample impurity concentration.

FIG. 16 schematically illustrates temporal functions including the concentration of impurities in a solution, exemplary diffusion step response functions, $f_{diff}(t)$, for a sensing region (solid line) and a reference region (dashed line) resulting from the step increase in the impurity concentration in solution, and the weighted average concentration of impurities, $C_{WG}(t)$, in the evanescent tail of the waveguide again for a sensing region (solid line) and a reference region (dashed line). The example reference region has a slower reponse to the concentration increase than the example sensing region. The examples also show that due to the sensing region partition coefficient being greater than the reference region partition coefficient, $K_{sens} > K_{ref}$, the weighted average concentration of impurities in the sensing region will always be greater than the weighted average concentration of impurities in the reference region.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the coupling structures and diffractive optical elements disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the coupling structures and diffractive optical elements disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of sensing a hydrocarbon, the method comprising:
   (A) coupling light into a waveguide comprising a core, a first cladding layer disposed on a first side of the core, and a second cladding layer disposed on a second side of the core, the second cladding layer comprising a continuous film of at least one hydrophobic polymer that defines (i) a first measurement region having a first surface with a first hydrophobicity and (ii) a second measurement region having a second surface with a second hydrophobicity greater than the first hydrophobicity;
   (B) exposing the second surface to a solution containing the hydrocarbon so as to cause a change in refractive index of the at least one hydrophobic polymer in the first measurement region via diffusion of the hydrocarbon into the at least one hydrophobic polymer; and
   (C) sensing a change in intensity of light evanescently coupled out of the waveguide in the second measurement region due to the change in refractive index in (B).

2. The method of claim 1, wherein the hydrocarbon comprises at least one of an aromatic hydrocarbon, a polyaromatic hydrocarbon, benzene, toluene, ethylbenzene, or xylene.

3. The method of claim 1, wherein (B) further comprises: allowing the solution containing the hydrocarbon to diffuse through an etched portion of the second surface.

4. The method of claim 1, wherein (B) further comprises: allowing the hydrocarbon to diffuse through a plurality of layers of the at least one hydrophobic polymer.

5. The method of claim 1, wherein (B) further comprises: exposing the first measurement region to the solution containing the hydrocarbon.

6. The method of claim 5, wherein (B) further comprises: inhibiting diffusion of the hydrocarbon into the first measurement region.

7. The method of claim 1, wherein (C) comprises sensing the change in intensity in less than about 10 minutes.

8. The method of claim 1, further comprising:(D) sensing an intensity of light evanescently coupled out of the waveguide in the first measurement region.

9. The method of claim 8, further comprising:
   (E) determining the presence of the hydrocarbon based on (i) the intensity of light sensed in (C) and (ii) the change in intensity of light sensed in (D).

* * * * *